(12) United States Patent
Katrana et al.

(10) Patent No.: US 8,377,066 B2
(45) Date of Patent: Feb. 19, 2013

(54) PATIENT-SPECIFIC ELBOW GUIDES AND ASSOCIATED METHODS

(75) Inventors: Nicholas J. Katrana, Fort Wayne, IN (US); Thomas M. Vanasse, Warsaw, IN (US); Robert Metzger, Wakarusa, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 126 days.

(21) Appl. No.: 12/888,005

(22) Filed: Sep. 22, 2010

(65) Prior Publication Data

US 2011/0015636 A1    Jan. 20, 2011

Related U.S. Application Data

(63) Continuation-in-part of application No. 12/714,023, filed on Feb. 26, 2010, now Pat. No. 8,241,293, which is a continuation-in-part of application No. 12/571,969, filed on Oct. 1, 2009, which is a continuation-in-part of application No. 12/389,901, (Continued)

(51) Int. Cl.
*A61F 2/46* (2006.01)

(52) U.S. Cl. .................................. 606/86 R

(58) Field of Classification Search .... 623/19.11–19.14, 623/20.11–20.15; 606/79–85, 86 R, 87–90, 606/96, 98, 99
See application file for complete search history.

(56) References Cited

U.S. PATENT DOCUMENTS

| | | | |
|---|---|---|---|
| 1,480,285 A | 1/1924 | Moore | |
| 2,181,746 A | 11/1939 | Siebrandt | |
| 2,407,845 A | 9/1946 | Nemeyer | |
| 2,618,913 A | 11/1952 | Plancon et al. | |
| 2,910,978 A | 11/1959 | Urist | |
| 3,840,904 A | 10/1974 | Tronzo | |
| 4,246,895 A | 1/1981 | Rehder | |
| 4,306,866 A | 12/1981 | Weissman | |
| 4,324,006 A | 4/1982 | Charnley | |
| 4,421,112 A | 12/1983 | Mains et al. | |
| 4,436,684 A | 3/1984 | White | |
| 4,475,549 A | 10/1984 | Oh | |
| 4,506,393 A | 3/1985 | Murphy | |
| 4,524,766 A | 6/1985 | Petersen | |
| 4,619,658 A | 10/1986 | Pappas et al. | |

(Continued)

FOREIGN PATENT DOCUMENTS

| CA | 2447694 A1 | 12/2002 |
|---|---|---|
| CA | 2501041 A1 | 4/2004 |

(Continued)

OTHER PUBLICATIONS

International Preliminary Report on Patentability mailed Aug. 25, 2011 for PCT/US2010/024073 filed Feb. 12, 2010, claiming benefit of U.S. Appl. No. 12/371,096, filed Feb. 13, 2009.

(Continued)

*Primary Examiner* — Alvin J. Stewart
(74) *Attorney, Agent, or Firm* — Harness, Dickey

(57) ABSTRACT

A patient-specific alignment guide includes a three-dimensional engagement surface customized in a pre-operating planning stage by computer imaging to closely mate and conform to a corresponding bone portion of a patient's elbow joint. The patient-specific alignment guide defines a first longitudinal guiding bore aligned with a reference axis associated with the elbow joint of patient when the alignment guide is mounted onto the corresponding bone portion.

19 Claims, 13 Drawing Sheets

Related U.S. Application Data filed on Feb. 20, 2009, now Pat. No. 8,133,234, which is a continuation-in-part of application No. 12/211,407, filed on Sep. 16, 2008, which is a continuation-in-part of application No. 12/039,849, filed on Feb. 29, 2008, now Pat. No. 8,282,646, which is a continuation-in-part of application No. 11/756,057, filed on May 31, 2007, now Pat. No. 8,092,465, said application No. 12/039,849 is a continuation-in-part of application No. 11/971,390, filed on Jan. 9, 2008, now Pat. No. 8,070,752, which is a continuation-in-part of application No. 11/363,548, filed on Feb. 27, 2006, now Pat. No. 7,780,672, said application No. 12/039,849 is a continuation-in-part of application No. 12/025,414, filed on Feb. 4, 2008, now Pat. No. 8,298,237, application No. 12/888,005, which is a continuation-in-part of application No. 12/872,663, filed on Aug. 31, 2010, application No. 12/888,005, which is a continuation-in-part of application No. 12/483,807, filed on Jun. 12, 2009, which is a continuation-in-part of application No. 12/371,096, filed on Feb. 13, 2009, which is a continuation-in-part of application No. 12/103,824, filed on Apr. 16, 2008.

(60) Provisional application No. 60/912,178, filed on Apr. 17, 2007, provisional application No. 61/310,752, filed on Mar. 5, 2010, provisional application No. 60/953,637, filed on Aug. 2, 2007, provisional application No. 60/812,694, filed on Jun. 9, 2006, provisional application No. 60/892,349, filed on Mar. 1, 2007, provisional application No. 60/911,297, filed on Apr. 12, 2007, provisional application No. 60/947,813, filed on Jul. 3, 2007, provisional application No. 60/953,620, filed on Aug. 2, 2007.

(56) References Cited

U.S. PATENT DOCUMENTS

| | | | |
|---|---|---|---|
| 4,621,630 | A | 11/1986 | Kenna |
| 4,632,111 | A | 12/1986 | Roche |
| 4,633,862 | A | 1/1987 | Petersen |
| 4,663,720 | A | 5/1987 | Duret et al. |
| 4,695,283 | A | 9/1987 | Aldinger |
| 4,696,292 | A | 9/1987 | Heiple |
| 4,703,751 | A | 11/1987 | Pohl |
| 4,704,686 | A | 11/1987 | Aldinger |
| 4,721,104 | A | 1/1988 | Kaufman et al. |
| 4,722,330 | A * | 2/1988 | Russell et al. ............... 606/88 |
| 4,778,474 | A | 10/1988 | Homsy |
| 4,800,874 | A | 1/1989 | David et al. |
| 4,821,213 | A | 4/1989 | Cline et al. |
| 4,822,365 | A | 4/1989 | Walker et al. |
| 4,841,975 | A | 6/1989 | Woolson |
| 4,846,161 | A | 7/1989 | Roger |
| 4,871,975 | A | 10/1989 | Nawata et al. |
| 4,893,619 | A | 1/1990 | Dale et al. |
| 4,896,663 | A | 1/1990 | Vandewalls |
| 4,927,422 | A | 5/1990 | Engelhardt |
| 4,936,862 | A | 6/1990 | Walker et al. |
| 4,952,213 | A | 8/1990 | Bowman et al. |
| 4,959,066 | A | 9/1990 | Dunn et al. |
| 4,976,737 | A | 12/1990 | Leake |
| 4,979,949 | A | 12/1990 | Matsen, III et al. |
| 4,985,037 | A | 1/1991 | Petersen |
| 5,002,579 | A | 3/1991 | Copf et al. |
| 5,007,936 | A | 4/1991 | Woolson |
| 5,030,221 | A | 7/1991 | Buechel et al. |
| 5,041,117 | A | 8/1991 | Engelhardt |
| 5,053,037 | A * | 10/1991 | Lackey ............... 606/79 |
| 5,053,039 | A | 10/1991 | Hofmann et al. |
| 5,086,401 | A | 2/1992 | Glassman et al. |
| 5,098,383 | A | 3/1992 | Hemmy et al. |
| 5,098,436 | A | 3/1992 | Ferrante et al. |
| 5,108,425 | A | 4/1992 | Hwang |
| 5,122,144 | A * | 6/1992 | Bert et al. ............... 606/88 |
| 5,129,908 | A | 7/1992 | Petersen |
| 5,129,909 | A * | 7/1992 | Sutherland ............... 606/88 |
| 5,133,760 | A | 7/1992 | Petersen et al. |
| 5,140,777 | A | 8/1992 | Ushiyama et al. |
| 5,150,304 | A | 9/1992 | Berchem et al. |
| 5,176,684 | A | 1/1993 | Ferrante et al. |
| 5,246,444 | A | 9/1993 | Schreiber |
| 5,258,032 | A | 11/1993 | Bertin |
| 5,261,915 | A | 11/1993 | Durlacher et al. |
| 5,274,565 | A | 12/1993 | Reuben |
| 5,299,288 | A | 3/1994 | Glassman et al. |
| 5,300,077 | A | 4/1994 | Howell |
| 5,320,625 | A | 6/1994 | Bertin |
| 5,342,366 | A | 8/1994 | Whiteside et al. |
| 5,344,423 | A | 9/1994 | Dietz et al. |
| 5,360,446 | A | 11/1994 | Kennedy |
| 5,368,858 | A | 11/1994 | Hunziker |
| 5,370,692 | A | 12/1994 | Fink et al. |
| 5,370,699 | A | 12/1994 | Hood et al. |
| 5,405,395 | A | 4/1995 | Coates |
| 5,408,409 | A | 4/1995 | Glassman et al. |
| 5,415,662 | A | 5/1995 | Ferrante et al. |
| 5,438,263 | A | 8/1995 | Dworkin et al. |
| 5,440,496 | A | 8/1995 | Andersson et al. |
| 5,448,489 | A | 9/1995 | Reuben |
| 5,449,360 | A | 9/1995 | Schreiber |
| 5,452,407 | A | 9/1995 | Crook |
| 5,454,816 | A | 10/1995 | Ashby |
| 5,472,415 | A | 12/1995 | King et al. |
| 5,474,559 | A | 12/1995 | Bertin et al. |
| 5,490,854 | A | 2/1996 | Fisher et al. |
| 5,496,324 | A | 3/1996 | Barnes |
| 5,507,833 | A | 4/1996 | Bohn |
| 5,514,519 | A | 5/1996 | Neckers |
| 5,520,695 | A | 5/1996 | Luckman |
| 5,527,317 | A | 6/1996 | Ashby et al. |
| 5,539,649 | A | 7/1996 | Walsh et al. |
| 5,540,695 | A | 7/1996 | Levy |
| 5,554,190 | A | 9/1996 | Draenert |
| 5,560,096 | A | 10/1996 | Stephens |
| 5,571,110 | A | 11/1996 | Matsen, III et al. |
| 5,578,037 | A | 11/1996 | Sanders et al. |
| 5,595,703 | A | 1/1997 | Swaelens et al. |
| 5,607,431 | A | 3/1997 | Dudasik et al. |
| 5,613,969 | A | 3/1997 | Jenkins, Jr. |
| 5,620,448 | A | 4/1997 | Puddu |
| 5,634,927 | A | 6/1997 | Houston et al. |
| 5,658,294 | A | 8/1997 | Sederholm |
| 5,662,656 | A | 9/1997 | White |
| 5,677,107 | A | 10/1997 | Neckers |
| 5,681,354 | A | 10/1997 | Eckhoff |
| 5,682,886 | A | 11/1997 | Delp et al. |
| 5,690,635 | A | 11/1997 | Matsen, III et al. |
| 5,702,460 | A | 12/1997 | Carls et al. |
| 5,704,941 | A | 1/1998 | Jacober et al. |
| 5,722,978 | A | 3/1998 | Jenkins, Jr. |
| 5,725,376 | A | 3/1998 | Poirier |
| 5,725,593 | A | 3/1998 | Caracciolo |
| 5,735,277 | A | 4/1998 | Schuster |
| 5,748,767 | A | 5/1998 | Raab |
| 5,749,875 | A | 5/1998 | Puddu |
| 5,749,876 | A | 5/1998 | Duvillier et al. |
| 5,762,125 | A | 6/1998 | Mastrorio |
| 5,768,134 | A | 6/1998 | Swaelens et al. |
| 5,769,092 | A | 6/1998 | Williamson, Jr. |
| 5,786,217 | A | 7/1998 | Tubo et al. |
| 5,792,143 | A | 8/1998 | Samuelson et al. |
| 5,798,924 | A | 8/1998 | Eufinger et al. |
| 5,799,055 | A | 8/1998 | Peshkin et al. |
| 5,860,981 | A | 1/1999 | Bertin et al. |
| 5,871,018 | A * | 2/1999 | Delp et al. ............... 128/898 |
| 5,876,456 | A | 3/1999 | Sederholm et al. |
| 5,879,398 | A | 3/1999 | Swarts et al. |
| 5,879,402 | A | 3/1999 | Lawes et al. |
| 5,880,976 | A | 3/1999 | DiGioia, III et al. |
| 5,885,297 | A | 3/1999 | Matsen, III |

| | | | |
|---|---|---|---|
| 5,885,298 A | 3/1999 | Herrington et al. | |
| 5,895,389 A | 4/1999 | Schenk et al. | |
| 5,899,907 A | 5/1999 | Johnson | |
| 5,901,060 A * | 5/1999 | Schall et al. ............... 700/98 | |
| 5,911,724 A | 6/1999 | Wehrli | |
| 5,925,049 A | 7/1999 | Gustilo et al. | |
| 5,942,370 A | 8/1999 | Neckers | |
| 5,967,777 A | 10/1999 | Klein et al. | |
| 5,976,149 A | 11/1999 | Masini | |
| 5,980,526 A | 11/1999 | Johnson et al. | |
| 6,033,415 A | 3/2000 | Mittelstadt et al. | |
| 6,059,789 A | 5/2000 | Dinger et al. | |
| 6,059,833 A | 5/2000 | Doets | |
| 6,086,593 A | 7/2000 | Bonutti | |
| 6,120,510 A | 9/2000 | Albrektsson et al. | |
| 6,120,544 A | 9/2000 | Grundei et al. | |
| 6,126,690 A | 10/2000 | Ateshian et al. | |
| 6,136,033 A | 10/2000 | Suemer | |
| 6,156,069 A | 12/2000 | Amstutz | |
| 6,161,080 A * | 12/2000 | Aouni-Ateshian et al. ...... 703/11 | |
| 6,187,010 B1 | 2/2001 | Masini | |
| 6,195,615 B1 | 2/2001 | Lysen | |
| 6,203,546 B1 | 3/2001 | MacMahon | |
| 6,205,411 B1 | 3/2001 | DiGioia, III et al. | |
| 6,206,927 B1 | 3/2001 | Fell et al. | |
| 6,254,604 B1 | 7/2001 | Howell | |
| 6,258,097 B1 | 7/2001 | Cook et al. | |
| 6,264,698 B1 | 7/2001 | Lawes et al. | |
| 6,273,891 B1 | 8/2001 | Masini | |
| 6,290,727 B1 | 9/2001 | Otto et al. | |
| 6,293,971 B1 | 9/2001 | Nelson et al. | |
| 6,312,473 B1 | 11/2001 | Oshida | |
| 6,319,285 B1 | 11/2001 | Chamier et al. | |
| 6,325,829 B1 | 12/2001 | Schmotzer | |
| 6,343,987 B2 | 2/2002 | Hayama et al. | |
| 6,354,011 B1 | 3/2002 | Albrecht | |
| 6,379,299 B1 | 4/2002 | Borodulin et al. | |
| 6,383,228 B1 | 5/2002 | Schmotzer | |
| 6,391,251 B1 | 5/2002 | Keicher et al. | |
| 6,395,005 B1 | 5/2002 | Lovell | |
| 6,427,698 B1 | 8/2002 | Yoon | |
| 6,459,948 B1 | 10/2002 | Ateshian et al. | |
| 6,463,351 B1 | 10/2002 | Clynch | |
| 6,475,243 B1 | 11/2002 | Sheldon et al. | |
| 6,482,236 B2 | 11/2002 | Habecker | |
| 6,488,715 B1 | 12/2002 | Pope et al. | |
| 6,503,255 B1 | 1/2003 | Albrektsson et al. | |
| 6,510,334 B1 | 1/2003 | Schuster et al. | |
| 6,514,259 B2 | 2/2003 | Picard et al. | |
| 6,517,583 B1 | 2/2003 | Pope et al. | |
| 6,520,964 B2 | 2/2003 | Tallarida et al. | |
| 6,533,737 B1 | 3/2003 | Brosseau et al. | |
| 6,547,823 B2 | 4/2003 | Scarborough et al. | |
| 6,554,837 B1 | 4/2003 | Hauri et al. | |
| 6,556,008 B2 | 4/2003 | Thesen | |
| 6,558,391 B2 | 5/2003 | Axelson, Jr. et al. | |
| 6,558,428 B2 | 5/2003 | Park | |
| 6,564,085 B2 | 5/2003 | Meaney et al. | |
| 6,567,681 B1 | 5/2003 | Lindequist | |
| 6,575,980 B1 | 6/2003 | Robie et al. | |
| 6,575,982 B1 | 6/2003 | Bonutti | |
| 6,591,581 B2 | 7/2003 | Schmieding | |
| 6,605,293 B1 | 8/2003 | Giordano et al. | |
| 6,622,567 B1 | 9/2003 | Hamel et al. | |
| 6,629,999 B1 | 10/2003 | Serafin, Jr. | |
| 6,641,617 B1 | 11/2003 | Merrill et al. | |
| 6,682,566 B2 | 1/2004 | Draenert | |
| 6,696,073 B2 | 2/2004 | Boyce et al. | |
| 6,697,664 B2 | 2/2004 | Kienzle III et al. | |
| 6,701,174 B1 | 3/2004 | Krause et al. | |
| 6,709,462 B2 | 3/2004 | Hanssen | |
| 6,711,431 B2 | 3/2004 | Pratt et al. | |
| 6,711,432 B1 | 3/2004 | Weiss et al. | |
| 6,712,856 B1 * | 3/2004 | Carignan et al. ........... 623/20.35 | |
| 6,716,249 B2 | 4/2004 | Hyde | |
| 6,725,077 B1 | 4/2004 | Balloni et al. | |
| 6,738,657 B1 | 5/2004 | Franklin et al. | |
| 6,740,092 B2 | 5/2004 | Lombardo et al. | |
| 6,749,638 B1 | 6/2004 | Saladino | |
| 6,750,653 B1 | 6/2004 | Zou et al. | |
| 6,772,026 B2 | 8/2004 | Bradbury et al. | |
| 6,780,190 B2 | 8/2004 | Maroney | |
| 6,786,930 B2 | 9/2004 | Biscup | |
| 6,799,066 B2 | 9/2004 | Steines et al. | |
| 6,823,871 B2 | 11/2004 | Schmieding | |
| 6,827,723 B2 | 12/2004 | Carson | |
| 6,887,247 B1 | 5/2005 | Couture et al. | |
| 6,905,514 B2 | 6/2005 | Carignan et al. | |
| 6,923,817 B2 | 8/2005 | Carson et al. | |
| 6,923,831 B2 | 8/2005 | Fell et al. | |
| 6,932,842 B1 | 8/2005 | Litschko et al. | |
| 6,942,475 B2 | 9/2005 | Ensign et al. | |
| 6,944,518 B2 | 9/2005 | Roose | |
| 6,945,976 B2 | 9/2005 | Ball et al. | |
| 6,953,480 B2 | 10/2005 | Mears et al. | |
| 6,960,216 B2 | 11/2005 | Kolb et al. | |
| 6,990,220 B2 | 1/2006 | Ellis et al. | |
| 7,029,479 B2 | 4/2006 | Tallarida et al. | |
| 7,042,222 B2 | 5/2006 | Zheng et al. | |
| 7,048,741 B2 | 5/2006 | Swanson | |
| 7,050,877 B2 | 5/2006 | Iseki et al. | |
| 7,060,074 B2 | 6/2006 | Rosa et al. | |
| 7,074,241 B2 | 7/2006 | McKinnon | |
| RE39,301 E | 9/2006 | Bertin | |
| 7,104,997 B2 | 9/2006 | Lionberger et al. | |
| 7,105,026 B2 | 9/2006 | Johnson et al. | |
| 7,115,131 B2 | 10/2006 | Engh et al. | |
| 7,141,053 B2 | 11/2006 | Rosa et al. | |
| 7,169,185 B2 | 1/2007 | Sidebotham | |
| 7,176,466 B2 | 2/2007 | Rousso et al. | |
| 7,184,814 B2 | 2/2007 | Lang et al. | |
| 7,198,628 B2 | 4/2007 | Ondrla et al. | |
| 7,218,232 B2 | 5/2007 | DiSilvestro et al. | |
| 7,239,908 B1 | 7/2007 | Alexander et al. | |
| 7,241,315 B2 | 7/2007 | Evans | |
| 7,255,702 B2 | 8/2007 | Serra et al. | |
| 7,258,701 B2 | 8/2007 | Aram et al. | |
| 7,275,218 B2 | 9/2007 | Petrella et al. | |
| 7,282,054 B2 | 10/2007 | Steffensmeier et al. | |
| 7,294,133 B2 | 11/2007 | Zink et al. | |
| 7,297,164 B2 | 11/2007 | Johnson et al. | |
| 7,309,339 B2 | 12/2007 | Cusick et al. | |
| 7,333,013 B2 | 2/2008 | Berger | |
| 7,335,231 B2 | 2/2008 | McLean | |
| 7,371,260 B2 | 5/2008 | Malinin | |
| 7,383,164 B2 * | 6/2008 | Aram et al. ............... 703/7 | |
| 7,385,498 B2 | 6/2008 | Dobosz | |
| 7,388,972 B2 | 6/2008 | Kitson | |
| 7,392,076 B2 | 6/2008 | Moctezuma de La Barrera | |
| 7,427,272 B2 | 9/2008 | Richard et al. | |
| 7,468,075 B2 | 12/2008 | Lang et al. | |
| 7,474,223 B2 | 1/2009 | Nycz et al. | |
| 7,488,325 B2 | 2/2009 | Qian | |
| 7,494,510 B2 | 2/2009 | Zweymuller | |
| 7,517,365 B2 | 4/2009 | Carignan et al. | |
| 7,527,631 B2 | 5/2009 | Maroney et al. | |
| 7,534,263 B2 | 5/2009 | Burdulis, Jr. et al. | |
| 7,542,791 B2 | 6/2009 | Mire et al. | |
| 7,559,931 B2 | 7/2009 | Stone | |
| 7,575,602 B2 | 8/2009 | Amirouche et al. | |
| 7,578,851 B2 | 8/2009 | Dong et al. | |
| 7,582,091 B2 | 9/2009 | Duncan et al. | |
| 7,591,821 B2 | 9/2009 | Kelman | |
| 7,601,155 B2 | 10/2009 | Petersen | |
| 7,604,639 B2 | 10/2009 | Swanson | |
| 7,611,516 B2 | 11/2009 | Maroney | |
| 7,618,451 B2 | 11/2009 | Berez et al. | |
| 7,621,915 B2 | 11/2009 | Frederick et al. | |
| 7,625,409 B2 | 12/2009 | Saltzman et al. | |
| 7,646,161 B2 | 1/2010 | Albu-Schaffer et al. | |
| 7,651,501 B2 | 1/2010 | Penenberg et al. | |
| 7,670,345 B2 | 3/2010 | Plassky et al. | |
| 7,682,398 B2 | 3/2010 | Croxton et al. | |
| 7,695,477 B2 * | 4/2010 | Creger et al. ............... 606/87 | |
| 7,695,521 B2 | 4/2010 | Ely et al. | |
| 7,699,847 B2 | 4/2010 | Sheldon et al. | |
| 7,704,253 B2 | 4/2010 | Bastian et al. | |
| 7,723,395 B2 | 5/2010 | Ringeisen et al. | |

| Patent/Publication | Date | Inventor |
|---|---|---|
| 7,780,740 B2 | 8/2010 | Steinberg |
| 7,794,466 B2 | 9/2010 | Merchant et al. |
| 7,794,467 B2 | 9/2010 | McGinley et al. |
| 7,794,504 B2 | 9/2010 | Case |
| 7,806,896 B1 | 10/2010 | Bonutti |
| 7,809,184 B2 | 10/2010 | Neubauer et al. |
| 7,819,925 B2 | 10/2010 | King et al. |
| 7,828,806 B2 | 11/2010 | Graf et al. |
| 7,879,109 B2 | 2/2011 | Borden et al. |
| 7,892,261 B2 | 2/2011 | Bonutti |
| 7,896,921 B2 | 3/2011 | Smith et al. |
| 7,935,119 B2 | 5/2011 | Ammann et al. |
| 7,935,150 B2 | 5/2011 | Carignan et al. |
| 7,938,861 B2 | 5/2011 | King et al. |
| 7,959,637 B2 | 6/2011 | Fox et al. |
| 7,962,196 B2 | 6/2011 | Tuma |
| 7,963,968 B2 | 6/2011 | Dees, Jr. |
| 7,967,823 B2 | 6/2011 | Ammann et al. |
| 7,967,868 B2 | 6/2011 | White et al. |
| 7,974,677 B2 | 7/2011 | Mire et al. |
| 7,981,158 B2 | 7/2011 | Fitz et al. |
| 7,993,353 B2 | 8/2011 | Rossner et al. |
| 8,062,301 B2 | 11/2011 | Ammann et al. |
| 8,070,752 B2 | 12/2011 | Metzger et al. |
| 8,083,745 B2 | 12/2011 | Lang et al. |
| 8,083,746 B2 | 12/2011 | Novak |
| 8,083,749 B2 | 12/2011 | Taber |
| 8,086,336 B2 | 12/2011 | Christensen |
| 8,092,465 B2 | 1/2012 | Metzger et al. |
| 8,133,230 B2 | 3/2012 | Stevens et al. |
| 8,137,406 B2 | 3/2012 | Novak et al. |
| 2001/0005797 A1 | 6/2001 | Barlow et al. |
| 2001/0011190 A1 | 8/2001 | Park |
| 2001/0054478 A1 | 12/2001 | Watanabe et al. |
| 2002/0007294 A1 | 1/2002 | Bradbury et al. |
| 2002/0059049 A1 | 5/2002 | Bradbury et al. |
| 2002/0082741 A1 | 6/2002 | Mazumder et al. |
| 2002/0087274 A1 | 7/2002 | Alexander et al. |
| 2002/0107522 A1 | 8/2002 | Picard et al. |
| 2002/0128872 A1 | 9/2002 | Giammattei |
| 2002/0147415 A1 | 10/2002 | Martelli |
| 2003/0009171 A1 | 1/2003 | Tornier |
| 2003/0009234 A1 | 1/2003 | Treacy et al. |
| 2003/0011624 A1 | 1/2003 | Ellis |
| 2003/0018338 A1 | 1/2003 | Axelson et al. |
| 2003/0039676 A1 | 2/2003 | Boyce et al. |
| 2003/0055502 A1 | 3/2003 | Lang et al. |
| 2003/0105526 A1 | 6/2003 | Bryant et al. |
| 2003/0109784 A1 | 6/2003 | Loh et al. |
| 2003/0120276 A1 | 6/2003 | Tallarida et al. |
| 2003/0139817 A1 | 7/2003 | Tuke et al. |
| 2003/0158606 A1 | 8/2003 | Coon et al. |
| 2003/0171757 A1 | 9/2003 | Coon et al. |
| 2003/0216669 A1* | 11/2003 | Lang et al. .................... 600/587 |
| 2004/0018144 A1 | 1/2004 | Briscoe |
| 2004/0030245 A1 | 2/2004 | Noble et al. |
| 2004/0054372 A1 | 3/2004 | Corden et al. |
| 2004/0068187 A1 | 4/2004 | Krause et al. |
| 2004/0092932 A1 | 5/2004 | Aubin et al. |
| 2004/0098133 A1* | 5/2004 | Carignan et al. ............ 623/20.35 |
| 2004/0102852 A1 | 5/2004 | Johnson et al. |
| 2004/0102866 A1 | 5/2004 | Harris et al. |
| 2004/0106926 A1 | 6/2004 | Leitner et al. |
| 2004/0115586 A1 | 6/2004 | Andreiko et al. |
| 2004/0122439 A1 | 6/2004 | Dwyer et al. |
| 2004/0128026 A1 | 7/2004 | Harris et al. |
| 2004/0133276 A1 | 7/2004 | Lang et al. |
| 2004/0138754 A1 | 7/2004 | Lang et al. |
| 2004/0143336 A1 | 7/2004 | Burkinshaw |
| 2004/0147927 A1 | 7/2004 | Tsougarakis et al. |
| 2004/0148026 A1 | 7/2004 | Bonutti |
| 2004/0153079 A1 | 8/2004 | Tsougarakis et al. |
| 2004/0153087 A1 | 8/2004 | Sanford et al. |
| 2004/0158254 A1 | 8/2004 | Eisermann |
| 2004/0162619 A1 | 8/2004 | Blaylock et al. |
| 2004/0167390 A1 | 8/2004 | Alexander et al. |
| 2004/0171924 A1 | 9/2004 | Mire et al. |
| 2004/0172137 A1 | 9/2004 | Blaylock et al. |
| 2004/0181144 A1 | 9/2004 | Cinquin et al. |
| 2004/0204644 A1 | 10/2004 | Tsougarakis et al. |
| 2004/0204760 A1* | 10/2004 | Fitz et al. .................... 623/14.12 |
| 2004/0212586 A1 | 10/2004 | Denny |
| 2004/0220583 A1 | 11/2004 | Pieczynski et al. |
| 2004/0236341 A1 | 11/2004 | Petersen |
| 2004/0236424 A1 | 11/2004 | Berez et al. |
| 2004/0243481 A1* | 12/2004 | Bradbury et al. ................ 705/26 |
| 2004/0254584 A1 | 12/2004 | Sarin et al. |
| 2005/0008887 A1 | 1/2005 | Haymann et al. |
| 2005/0010300 A1 | 1/2005 | Disilvestro et al. |
| 2005/0015022 A1 | 1/2005 | Richard et al. |
| 2005/0019664 A1 | 1/2005 | Matsumoto |
| 2005/0027303 A1 | 2/2005 | Lionberger et al. |
| 2005/0027361 A1 | 2/2005 | Reiley |
| 2005/0043806 A1 | 2/2005 | Cook et al. |
| 2005/0043837 A1 | 2/2005 | Rubbert et al. |
| 2005/0049524 A1 | 3/2005 | Lefevre et al. |
| 2005/0049603 A1 | 3/2005 | Calton et al. |
| 2005/0059873 A1 | 3/2005 | Glozman et al. |
| 2005/0060040 A1 | 3/2005 | Auxepaules et al. |
| 2005/0065628 A1 | 3/2005 | Roose |
| 2005/0070897 A1 | 3/2005 | Petersen |
| 2005/0071015 A1 | 3/2005 | Sekel |
| 2005/0075641 A1 | 4/2005 | Singhatat et al. |
| 2005/0096535 A1 | 5/2005 | de la Barrera |
| 2005/0113841 A1 | 5/2005 | Sheldon et al. |
| 2005/0113846 A1 | 5/2005 | Carson |
| 2005/0119664 A1* | 6/2005 | Carignan et al. ................. 606/96 |
| 2005/0131662 A1 | 6/2005 | Ascenzi et al. |
| 2005/0137708 A1 | 6/2005 | Clark |
| 2005/0148843 A1 | 7/2005 | Roose |
| 2005/0149042 A1 | 7/2005 | Metzger |
| 2005/0171545 A1 | 8/2005 | Walsh et al. |
| 2005/0177245 A1 | 8/2005 | Leatherbury et al. |
| 2005/0203536 A1 | 9/2005 | Laffargue et al. |
| 2005/0203540 A1 | 9/2005 | Broyles |
| 2005/0216305 A1 | 9/2005 | Funderud |
| 2005/0222573 A1 | 10/2005 | Branch et al. |
| 2005/0234461 A1* | 10/2005 | Burdulis et al. ................. 606/79 |
| 2005/0234468 A1 | 10/2005 | Carson |
| 2005/0240267 A1 | 10/2005 | Randall et al. |
| 2005/0244239 A1 | 11/2005 | Shimp |
| 2005/0245934 A1 | 11/2005 | Tuke et al. |
| 2005/0245936 A1 | 11/2005 | Tuke et al. |
| 2005/0251147 A1 | 11/2005 | Novak |
| 2005/0267353 A1 | 12/2005 | Marquart et al. |
| 2005/0267485 A1 | 12/2005 | Cordes et al. |
| 2005/0267584 A1 | 12/2005 | Burdulis et al. |
| 2005/0273114 A1 | 12/2005 | Novak |
| 2005/0283252 A1 | 12/2005 | Coon et al. |
| 2005/0283253 A1 | 12/2005 | Coon et al. |
| 2006/0004284 A1 | 1/2006 | Grunschlager et al. |
| 2006/0015120 A1 | 1/2006 | Richard et al. |
| 2006/0030853 A1 | 2/2006 | Haines |
| 2006/0038520 A1 | 2/2006 | Negoro et al. |
| 2006/0052725 A1 | 3/2006 | Santilli |
| 2006/0058803 A1 | 3/2006 | Cuckler et al. |
| 2006/0058884 A1 | 3/2006 | Aram et al. |
| 2006/0058886 A1 | 3/2006 | Wozencroft |
| 2006/0089621 A1 | 4/2006 | Fard |
| 2006/0093988 A1 | 5/2006 | Swaelens et al. |
| 2006/0094951 A1 | 5/2006 | Dean et al. |
| 2006/0095044 A1 | 5/2006 | Grady et al. |
| 2006/0100832 A1 | 5/2006 | Bowman |
| 2006/0111722 A1 | 5/2006 | Bouadi |
| 2006/0122616 A1 | 6/2006 | Bennett et al. |
| 2006/0136058 A1 | 6/2006 | Pietrzak |
| 2006/0142657 A1 | 6/2006 | Quaid et al. |
| 2006/0155380 A1 | 7/2006 | Clemow et al. |
| 2006/0161167 A1 | 7/2006 | Myers et al. |
| 2006/0172263 A1 | 8/2006 | Quadling et al. |
| 2006/0178497 A1 | 8/2006 | Gevaert et al. |
| 2006/0184177 A1 | 8/2006 | Echeverri |
| 2006/0190086 A1 | 8/2006 | Clemow et al. |
| 2006/0195198 A1 | 8/2006 | James |
| 2006/0204932 A1 | 9/2006 | Haymann et al. |
| 2006/0210644 A1 | 9/2006 | Levin |
| 2006/0217808 A1 | 9/2006 | Novak et al. |
| 2006/0235421 A1 | 10/2006 | Rosa et al. |

| Publication No. | Date | Inventor(s) | Class |
|---|---|---|---|
| 2006/0271058 A1 | 11/2006 | Ashton et al. | |
| 2006/0276796 A1* | 12/2006 | Creger et al. | 606/79 |
| 2006/0276797 A1 | 12/2006 | Botimer | |
| 2006/0287733 A1 | 12/2006 | Bonutti | |
| 2007/0015995 A1* | 1/2007 | Lang et al. | 600/407 |
| 2007/0016209 A1* | 1/2007 | Ammann et al. | 606/79 |
| 2007/0027680 A1 | 2/2007 | Ashley et al. | |
| 2007/0066917 A1 | 3/2007 | Hodorek et al. | |
| 2007/0073137 A1 | 3/2007 | Schoenefeld | |
| 2007/0083214 A1 | 4/2007 | Duncan et al. | |
| 2007/0083266 A1 | 4/2007 | Lang | |
| 2007/0100258 A1 | 5/2007 | Shoham et al. | |
| 2007/0100450 A1 | 5/2007 | Hodorek | |
| 2007/0100462 A1 | 5/2007 | Lang et al. | |
| 2007/0118055 A1 | 5/2007 | McCombs | |
| 2007/0118243 A1 | 5/2007 | Schroeder et al. | |
| 2007/0150068 A1 | 6/2007 | Dong et al. | |
| 2007/0156066 A1 | 7/2007 | McGinley et al. | |
| 2007/0156171 A1 | 7/2007 | Lang et al. | |
| 2007/0162038 A1 | 7/2007 | Tuke | |
| 2007/0162039 A1 | 7/2007 | Wozencroft | |
| 2007/0173946 A1 | 7/2007 | Bonutti | |
| 2007/0173948 A1 | 7/2007 | Meridew et al. | |
| 2007/0185498 A2 | 8/2007 | Lavallee | |
| 2007/0191962 A1 | 8/2007 | Jones et al. | |
| 2007/0198022 A1 | 8/2007 | Lang et al. | |
| 2007/0203430 A1 | 8/2007 | Lang et al. | |
| 2007/0203605 A1 | 8/2007 | Melton et al. | |
| 2007/0219639 A1 | 9/2007 | Otto et al. | |
| 2007/0219640 A1 | 9/2007 | Steinberg | |
| 2007/0224238 A1 | 9/2007 | Mansmann et al. | |
| 2007/0226986 A1 | 10/2007 | Park et al. | |
| 2007/0233121 A1 | 10/2007 | Carson et al. | |
| 2007/0233136 A1 | 10/2007 | Wozencroft | |
| 2007/0233140 A1 | 10/2007 | Metzger et al. | |
| 2007/0233141 A1 | 10/2007 | Park et al. | |
| 2007/0233269 A1 | 10/2007 | Steines et al. | |
| 2007/0233272 A1 | 10/2007 | Boyce et al. | |
| 2007/0238069 A1 | 10/2007 | Lovald et al. | |
| 2007/0239282 A1 | 10/2007 | Caylor et al. | |
| 2007/0239481 A1 | 10/2007 | DiSilvestro et al. | |
| 2007/0250169 A1 | 10/2007 | Lang | |
| 2007/0253617 A1 | 11/2007 | Arata et al. | |
| 2007/0255288 A1 | 11/2007 | Mahfouz et al. | |
| 2007/0255412 A1 | 11/2007 | Hajaj et al. | |
| 2007/0262867 A1 | 11/2007 | Westrick et al. | |
| 2007/0272747 A1 | 11/2007 | Woods et al. | |
| 2007/0276224 A1 | 11/2007 | Lang et al. | |
| 2007/0276400 A1 | 11/2007 | Moore et al. | |
| 2007/0276501 A1 | 11/2007 | Betz et al. | |
| 2007/0288030 A1* | 12/2007 | Metzger et al. | 606/87 |
| 2008/0009952 A1 | 1/2008 | Hodge | |
| 2008/0015604 A1 | 1/2008 | Collazo | |
| 2008/0015605 A1 | 1/2008 | Collazo | |
| 2008/0021299 A1* | 1/2008 | Meulink | 600/407 |
| 2008/0021494 A1 | 1/2008 | Schmelzeisen-Redeker et al. | |
| 2008/0021567 A1 | 1/2008 | Meulink et al. | |
| 2008/0027563 A1 | 1/2008 | Johnson et al. | |
| 2008/0033442 A1 | 2/2008 | Amiot et al. | |
| 2008/0051799 A1 | 2/2008 | Bonutti | |
| 2008/0051910 A1 | 2/2008 | Kammerzell et al. | |
| 2008/0058945 A1 | 3/2008 | Hajaj et al. | |
| 2008/0058947 A1 | 3/2008 | Earl et al. | |
| 2008/0062183 A1 | 3/2008 | Swaelens | |
| 2008/0065225 A1 | 3/2008 | Wasielewski et al. | |
| 2008/0112996 A1 | 5/2008 | Harlow et al. | |
| 2008/0114370 A1 | 5/2008 | Schoenefeld | |
| 2008/0133022 A1 | 6/2008 | Caylor | |
| 2008/0140209 A1 | 6/2008 | Iannotti et al. | |
| 2008/0140213 A1 | 6/2008 | Ammann et al. | |
| 2008/0146969 A1 | 6/2008 | Kurtz | |
| 2008/0147072 A1 | 6/2008 | Park et al. | |
| 2008/0161815 A1 | 7/2008 | Schoenefeld et al. | |
| 2008/0172125 A1 | 7/2008 | Ek | |
| 2008/0195099 A1 | 8/2008 | Minas | |
| 2008/0195107 A1 | 8/2008 | Cuckler et al. | |
| 2008/0195108 A1 | 8/2008 | Bhatnagar et al. | |
| 2008/0195216 A1 | 8/2008 | Philipp | |
| 2008/0200926 A1 | 8/2008 | Verard et al. | |
| 2008/0208200 A1 | 8/2008 | Crofford | |
| 2008/0208353 A1 | 8/2008 | Kumar et al. | |
| 2008/0215059 A1* | 9/2008 | Carignan et al. | 606/96 |
| 2008/0230422 A1 | 9/2008 | Pleil et al. | |
| 2008/0234664 A1 | 9/2008 | May et al. | |
| 2008/0234683 A1 | 9/2008 | May | |
| 2008/0234685 A1 | 9/2008 | Gjerde | |
| 2008/0234833 A1 | 9/2008 | Bandoh et al. | |
| 2008/0243127 A1 | 10/2008 | Lang et al. | |
| 2008/0255674 A1 | 10/2008 | Rahaman et al. | |
| 2008/0257363 A1 | 10/2008 | Schoenefeld et al. | |
| 2008/0262500 A1 | 10/2008 | Collazo | |
| 2008/0262624 A1 | 10/2008 | White et al. | |
| 2008/0269906 A1 | 10/2008 | Iannotti et al. | |
| 2008/0275452 A1 | 11/2008 | Lang et al. | |
| 2008/0281328 A1 | 11/2008 | Lang et al. | |
| 2008/0281329 A1 | 11/2008 | Fitz et al. | |
| 2008/0281426 A1 | 11/2008 | Fitz et al. | |
| 2008/0287954 A1* | 11/2008 | Kunz et al. | 606/87 |
| 2008/0294266 A1 | 11/2008 | Steinberg | |
| 2008/0300600 A1 | 12/2008 | Guelat et al. | |
| 2008/0306558 A1 | 12/2008 | Hakki | |
| 2008/0312659 A1 | 12/2008 | Metzger et al. | |
| 2008/0319448 A1 | 12/2008 | Lavallee et al. | |
| 2009/0012526 A1 | 1/2009 | Fletcher | |
| 2009/0018546 A1 | 1/2009 | Daley | |
| 2009/0018666 A1 | 1/2009 | Grundei et al. | |
| 2009/0024131 A1 | 1/2009 | Metzger et al. | |
| 2009/0043556 A1 | 2/2009 | Axelson et al. | |
| 2009/0076371 A1 | 3/2009 | Lang et al. | |
| 2009/0076512 A1 | 3/2009 | Ammann et al. | |
| 2009/0082770 A1 | 3/2009 | Worner et al. | |
| 2009/0087276 A1 | 4/2009 | Rose | |
| 2009/0088674 A1 | 4/2009 | Caillouette et al. | |
| 2009/0088753 A1 | 4/2009 | Aram et al. | |
| 2009/0088754 A1* | 4/2009 | Aker et al. | 606/79 |
| 2009/0088755 A1* | 4/2009 | Aker et al. | 606/79 |
| 2009/0088758 A1* | 4/2009 | Bennett | 606/82 |
| 2009/0088759 A1* | 4/2009 | Aram et al. | 606/87 |
| 2009/0088760 A1* | 4/2009 | Aram et al. | 606/87 |
| 2009/0088761 A1* | 4/2009 | Roose et al. | 606/87 |
| 2009/0088763 A1* | 4/2009 | Aram et al. | 606/88 |
| 2009/0088865 A1 | 4/2009 | Brehm | |
| 2009/0088866 A1 | 4/2009 | Case | |
| 2009/0089034 A1 | 4/2009 | Penney et al. | |
| 2009/0089081 A1 | 4/2009 | Haddad | |
| 2009/0093815 A1 | 4/2009 | Fletcher et al. | |
| 2009/0093816 A1* | 4/2009 | Roose et al. | 606/87 |
| 2009/0096613 A1 | 4/2009 | Westrick | |
| 2009/0099567 A1* | 4/2009 | Zajac | 606/79 |
| 2009/0105837 A1 | 4/2009 | Lafosse et al. | |
| 2009/0118736 A1 | 5/2009 | Kreuzer | |
| 2009/0131941 A1 | 5/2009 | Park et al. | |
| 2009/0131942 A1* | 5/2009 | Aker et al. | 606/88 |
| 2009/0138020 A1 | 5/2009 | Park et al. | |
| 2009/0149965 A1 | 6/2009 | Quaid | |
| 2009/0149977 A1 | 6/2009 | Schendel | |
| 2009/0151736 A1 | 6/2009 | Belcher et al. | |
| 2009/0157083 A1 | 6/2009 | Park et al. | |
| 2009/0163922 A1 | 6/2009 | Meridew et al. | |
| 2009/0163923 A1 | 6/2009 | Flett et al. | |
| 2009/0164024 A1 | 6/2009 | Rudan et al. | |
| 2009/0177282 A1 | 7/2009 | Bureau et al. | |
| 2009/0187193 A1 | 7/2009 | Maroney et al. | |
| 2009/0209884 A1 | 8/2009 | Van Vorhis et al. | |
| 2009/0209961 A1 | 8/2009 | Ferrante et al. | |
| 2009/0222014 A1* | 9/2009 | Bojarski et al. | 606/88 |
| 2009/0222015 A1* | 9/2009 | Park et al. | 606/89 |
| 2009/0222016 A1* | 9/2009 | Park et al. | 606/89 |
| 2009/0222103 A1 | 9/2009 | Fitz et al. | |
| 2009/0228016 A1 | 9/2009 | Alvarez et al. | |
| 2009/0234360 A1 | 9/2009 | Alexander | |
| 2009/0248044 A1 | 10/2009 | Amiot et al. | |
| 2009/0254093 A1 | 10/2009 | White et al. | |
| 2009/0254367 A1* | 10/2009 | Belcher et al. | 705/2 |
| 2009/0270868 A1 | 10/2009 | Park et al. | |
| 2009/0274350 A1 | 11/2009 | Pavlovskaia et al. | |
| 2009/0306676 A1 | 12/2009 | Lang et al. | |
| 2009/0307893 A1 | 12/2009 | Burdulis, Jr. et al. | |

| | | |
|---|---|---|
| 2009/0318836 A1 | 12/2009 | Stone et al. |
| 2010/0016984 A1 | 1/2010 | Trabish |
| 2010/0016986 A1 | 1/2010 | Trabish |
| 2010/0023015 A1* | 1/2010 | Park .................................. 606/87 |
| 2010/0030231 A1 | 2/2010 | Revie et al. |
| 2010/0042105 A1* | 2/2010 | Park et al. ........................ 606/87 |
| 2010/0049195 A1* | 2/2010 | Park et al. ........................ 606/87 |
| 2010/0076439 A1 | 3/2010 | Hatch |
| 2010/0076505 A1 | 3/2010 | Borja |
| 2010/0076563 A1 | 3/2010 | Otto et al. |
| 2010/0076571 A1 | 3/2010 | Hatch |
| 2010/0082034 A1 | 4/2010 | Remia |
| 2010/0082035 A1 | 4/2010 | Keefer |
| 2010/0087829 A1* | 4/2010 | Metzger et al. .................. 606/96 |
| 2010/0094295 A1 | 4/2010 | Schnieders et al. |
| 2010/0105011 A1 | 4/2010 | Karkar et al. |
| 2010/0121335 A1 | 5/2010 | Penenberg et al. |
| 2010/0137869 A1 | 6/2010 | Borja et al. |
| 2010/0137924 A1 | 6/2010 | Tuke et al. |
| 2010/0145343 A1 | 6/2010 | Johnson et al. |
| 2010/0145344 A1 | 6/2010 | Jordan et al. |
| 2010/0152782 A1* | 6/2010 | Stone et al. .................. 606/280 |
| 2010/0160917 A1 | 6/2010 | Fitz et al. |
| 2010/0168754 A1 | 7/2010 | Fitz et al. |
| 2010/0168857 A1 | 7/2010 | Hatch |
| 2010/0179663 A1 | 7/2010 | Steinberg |
| 2010/0185202 A1 | 7/2010 | Lester et al. |
| 2010/0191244 A1* | 7/2010 | White et al. ..................... 606/88 |
| 2010/0212138 A1* | 8/2010 | Carroll et al. .................... 29/446 |
| 2010/0217109 A1 | 8/2010 | Belcher |
| 2010/0217270 A1 | 8/2010 | Polinski et al. |
| 2010/0217336 A1 | 8/2010 | Crawford et al. |
| 2010/0217338 A1* | 8/2010 | Carroll et al. ............... 606/86 R |
| 2010/0228257 A1 | 9/2010 | Bonutti |
| 2010/0249657 A1 | 9/2010 | Nycz et al. |
| 2010/0249796 A1 | 9/2010 | Nycz |
| 2010/0262150 A1 | 10/2010 | Lian |
| 2010/0274253 A1 | 10/2010 | Ure |
| 2010/0281678 A1 | 11/2010 | Burdulis, Jr. et al. |
| 2010/0286700 A1 | 11/2010 | Snider et al. |
| 2010/0292743 A1 | 11/2010 | Singhal et al. |
| 2010/0305574 A1 | 12/2010 | Fitz et al. |
| 2010/0324692 A1* | 12/2010 | Uthgenannt et al. ........ 623/20.35 |
| 2011/0004317 A1 | 1/2011 | Hacking et al. |
| 2011/0014267 A1* | 1/2011 | Everland et al. .............. 424/426 |
| 2011/0015636 A1* | 1/2011 | Katrana et al. ................. 606/87 |
| 2011/0015639 A1* | 1/2011 | Metzger et al. ................. 606/91 |
| 2011/0015752 A1 | 1/2011 | Meridew |
| 2011/0029091 A1 | 2/2011 | Bojarski et al. |
| 2011/0029116 A1* | 2/2011 | Jordan et al. ..................... 700/98 |
| 2011/0035012 A1 | 2/2011 | Linares |
| 2011/0040303 A1 | 2/2011 | Iannotti |
| 2011/0040334 A1 | 2/2011 | Kaes et al. |
| 2011/0046735 A1 | 2/2011 | Metzger et al. |
| 2011/0054478 A1 | 3/2011 | Vanasse et al. |
| 2011/0066193 A1 | 3/2011 | Lang et al. |
| 2011/0066245 A1 | 3/2011 | Lang et al. |
| 2011/0071528 A1 | 3/2011 | Carson |
| 2011/0071529 A1 | 3/2011 | Carson |
| 2011/0071530 A1 | 3/2011 | Carson |
| 2011/0071532 A1 | 3/2011 | Carson |
| 2011/0071533 A1 | 3/2011 | Metzger et al. |
| 2011/0092804 A1 | 4/2011 | Schoenefeld et al. |
| 2011/0093086 A1 | 4/2011 | Witt et al. |
| 2011/0106254 A1 | 5/2011 | Abel et al. |
| 2011/0125264 A1 | 5/2011 | Bagga et al. |
| 2011/0151027 A1 | 6/2011 | Clineff et al. |
| 2011/0151259 A1 | 6/2011 | Jarman-Smith et al. |
| 2011/0153025 A1 | 6/2011 | McMinn |
| 2011/0160736 A1 | 6/2011 | Meridew et al. |
| 2011/0160867 A1 | 6/2011 | Meridew et al. |
| 2011/0166578 A1* | 7/2011 | Stone et al. ...................... 606/88 |
| 2011/0172672 A1* | 7/2011 | Dubeau et al. .................. 606/87 |
| 2011/0184419 A1 | 7/2011 | Meridew et al. |
| 2011/0184526 A1* | 7/2011 | White et al. ............... 623/20.32 |
| 2011/0190899 A1 | 8/2011 | Pierce et al. |
| 2011/0190901 A1 | 8/2011 | Weissberg et al. |
| 2011/0213376 A1 | 9/2011 | Maxson et al. |
| 2011/0214279 A1 | 9/2011 | Park et al. |
| 2011/0218545 A1* | 9/2011 | Catanzarite et al. ............ 606/96 |
| 2011/0224674 A1* | 9/2011 | White et al. ..................... 606/91 |
| 2011/0257657 A1 | 10/2011 | Turner et al. |
| 2012/0010619 A1 | 1/2012 | Barsoum |
| 2012/0010710 A1 | 1/2012 | Frigg |
| 2012/0010711 A1 | 1/2012 | Antonyshyn et al. |
| 2012/0053697 A1* | 3/2012 | Palmer et al. .............. 623/20.12 |
| 2012/0071883 A1* | 3/2012 | Lang et al. ....................... 606/88 |
| 2012/0078258 A1* | 3/2012 | Lo et al. ........................... 606/87 |
| 2012/0078263 A1* | 3/2012 | Parisi et al. ..................... 606/89 |

FOREIGN PATENT DOCUMENTS

| | | |
|---|---|---|
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2588907 A1 | 6/2006 |
| CA | 2590534 A1 | 6/2006 |
| CN | 1630495 A | 6/2005 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| DE | 3447365 A1 | 7/1986 |
| DE | 04219939 A1 | 12/1993 |
| DE | 4421153 A1 | 12/1995 |
| DE | 102009028503 A1 | 2/2011 |
| EP | 0114505 A1 | 8/1984 |
| EP | 0326768 A2 | 8/1989 |
| EP | 0579868 A2 | 1/1994 |
| EP | 0645984 A1 | 4/1995 |
| EP | 0650706 A1 | 5/1995 |
| EP | 0916324 A2 | 5/1999 |
| EP | 1321107 A1 | 6/2003 |
| EP | 1327424 A1 | 7/2003 |
| EP | 1437102 A1 | 7/2004 |
| EP | 01486900 A1 | 12/2004 |
| EP | 1852072 A2 | 7/2007 |
| EP | 1832239 A1 | 9/2007 |
| FR | 2659226 A1 | 9/1991 |
| FR | 2721195 A1 | 12/1995 |
| FR | 2768916 A1 | 4/1999 |
| GB | 2094590 A | 9/1982 |
| GB | 2197790 A | 6/1988 |
| GB | 2442441 A | 4/2008 |
| JP | 59157715 A | 9/1984 |
| JP | 60231208 A | 11/1985 |
| KR | 20050072500 A | 7/2005 |
| KR | 20050084024 A | 8/2005 |
| RU | 2083179 C1 | 7/1997 |
| RU | 2113182 C1 | 6/1998 |
| RU | 2125835 C1 | 2/1999 |
| RU | 2138223 C1 | 9/1999 |
| RU | 2175534 C2 | 11/2001 |
| RU | 2187975 C1 | 8/2002 |
| TW | 231755 | 5/2005 |
| WO | WO-8807840 A1 | 10/1988 |
| WO | WO-9107139 A1 | 5/1991 |
| WO | WO-9325157 A1 | 12/1993 |
| WO | WO-9528688 A1 | 10/1995 |
| WO | WO-9952473 A1 | 10/1999 |
| WO | WO-9959106 A1 | 11/1999 |
| WO | WO-0170142 A1 | 9/2001 |
| WO | WO-0184479 A1 | 11/2001 |
| WO | WO-0217821 A2 | 3/2002 |
| WO | WO-0226145 | 4/2002 |
| WO | WO-0236024 A1 | 5/2002 |
| WO | WO-02096268 A2 | 12/2002 |
| WO | WO-03051210 A2 | 6/2003 |
| WO | WO-03051211 A1 | 6/2003 |
| WO | WO-2004032806 A1 | 4/2004 |
| WO | WO-2004049981 A2 | 6/2004 |
| WO | WO-2004051301 A2 | 6/2004 |
| WO | WO-2004078069 A2 | 9/2004 |
| WO | WO-2005051239 A1 | 6/2005 |
| WO | WO-2005051240 A1 | 6/2005 |
| WO | WO-2005077039 A2 | 8/2005 |

| | | | |
|---|---|---|---|
| WO | WO-2006058057 A2 | 6/2006 |
| WO | WO-2006060795 A1 | 6/2006 |
| WO | WO-2006092600 A1 | 9/2006 |
| WO | WO-2006127486 A2 | 11/2006 |
| WO | WO-2006134345 A1 | 12/2006 |
| WO | WO-2006136955 A1 | 12/2006 |
| WO | WO-2007041375 A2 | 4/2007 |
| WO | WO-2007053572 A2 | 5/2007 |
| WO | WO-2007062079 A2 | 5/2007 |
| WO | WO-2007092841 A2 | 8/2007 |
| WO | WO-2007137327 A1 | 12/2007 |
| WO | WO-2007145937 A2 | 12/2007 |
| WO | WO-2008014618 A1 | 2/2008 |
| WO | WO-2008021494 A2 | 2/2008 |
| WO | WO-2008040961 A1 | 4/2008 |
| WO | WO-2008044055 A1 | 4/2008 |
| WO | WO-2008101090 A2 | 8/2008 |
| WO | WO-2008109751 A1 | 9/2008 |
| WO | WO-2008112996 A1 | 9/2008 |
| WO | WO-2008140748 A1 | 11/2008 |
| WO | WO-2009001083 A1 | 12/2008 |
| WO | WO-2009025783 A1 | 2/2009 |
| WO | WO-2009129063 A1 | 10/2009 |
| WO | WO-2009129067 A1 | 10/2009 |
| WO | WO-2010033431 A1 | 3/2010 |
| WO | WO-2010093902 A1 | 8/2010 |
| WO | WO-2010096557 A2 | 8/2010 |
| WO | WO-2010144705 A1 | 12/2010 |
| WO | WO-2010148103 A1 | 12/2010 |
| WO | WO-2011018458 A1 | 2/2011 |
| WO | WO-2011041398 A1 | 4/2011 |
| WO | WO-2011106711 A1 | 9/2011 |
| WO | WO-2011109260 A1 | 9/2011 |
| WO | WO-2012006444 A2 | 1/2012 |
| WO | WO-2012061042 A1 | 5/2012 |

OTHER PUBLICATIONS

International Preliminary Report on Patentability mailed Sep. 1, 2011 for PCT/US2010/024579 claiming benefit of U.S. Appl. No. 12/389,930, filed Feb. 20, 2009.
International Preliminary Report on Patentability mailed Sep. 1, 2011 for PCT/US2010/024584 claiming benefit of U.S. Appl. No. 12/389,901, filed Feb. 20, 2009.
International Search Report and Written Opinion mailed Aug. 9, 2011 for PCT/US2011/026333 claiming benefit of U.S. Appl. No. 12/714,023, filed Feb. 26, 2010.
Great Britain Search Report mailed Dec. 21, 2011 for GB1116054.6, claiming benefit of U.S. Appl. No. 12/888,005, filed Sep. 22, 2010.
International Preliminary Report and Written Opinion mailed Jan. 5, 2012 for PCT/US2010/038845 claiming benefit of U.S. Appl. No. 12/486,992, filed Jun. 18, 2009.
International Preliminary Report on Patentability and Written Opinion mailed Dec. 22, 2011 for PCT/US2010/038177 claiming benefit of U.S. Appl. No. 12/483,807, filed Jun. 12, 2009.
International Search Report mailed Nov. 30, 2010 for PCT/EP2010/061630 filed Aug. 10, 2010 claiming benefit of DE102009028503.2 filed Aug. 13, 2009.
Supplementary European Search Report mailed Nov. 15, 2011 for EP07809326, which claims benefit of PCT/US2007/013223, filed Jun. 5, 2007; which claims priority to U.S. Appl. No. 11/756,057, filed May 31, 2007.
"Amazing Precision. Beautiful Results. The next evolution of MAKOplasty® is here," brochure. (Feb. 2009) MAKO Surgical Corp. 6 pages.
"Ascent Total Knee System," brochure. Biomet, Inc. (1999) 16 sheets.
"Customized Patient Instruments, Patient specific instruments for patient specific needs," brochure. (2008) DePuy Orthopaedics, Inc. 14 sheets.
"Customized Patient Instruments, Primary Cruciate Retaining Surgical Technique for use with the Sigma® Knee System Utilizing Specialist® 2 Instrumentation," brochure. (2008) DePuy Orthopaedics, Inc. pp. 1-23.
"Discovery® Elbow System Surgical Technique," brochure. Biomet Orthopedics, Inc. (2008) pp. 1-25.

"Discovery® Elbow System," brochure. Biomet Orthopedics, Inc. (2007) 3 sheets.
"Hipsextant Instructions of Use." (2011) Surgical Planning Associates, Inc. 19 pages.
"Knee tensor combined with laser femoral head locator," Research Disclosure. Jul. 2006. No. 507; p. 903.
"Method for constructing an allograft sleeve." Research Disclosure (Dec. 2003) No. 476, p. 1294.
"OSS™ Orthopaedic Salvage System, Femoral/Tibial Augmentation," brochure. Biomet Orthopedics, Inc., (2003) pp. 1-8 (12 sheets).
"Patient Matched PMI Implants, C.A.M.R.A. 3-D Imaging," brochure, Biomet, Inc. (1990) 6 pages.
"Regenerex® Tibial Cone Augment, Surgical Technique Addendum to the Vanguard® SSK Revision System," brochure. Biomet® Orthopedics. (2009) pp. 1-8 (12 sheets).
"Signature™ Personalized Patient Care, Surgical Technique Addendum to the Vanguard Knee System" brochure. Biomet® Orthopedics, Inc. (2009) pp. 1-8.
"TruMatch™ Personalized knee replacement solutions," tri-fold brochure. (2009) SIGMA® DePuy Orthopaedics, Inc. 2 pages.
"Vanguard® PFR Partial Knee Patellofemoral Replacement System," Surgical Technique brochure. Biomet Orthopaedics, (2010) pp. 1-25.
"Zimmer® UniSpacer® Knee System," brochure. (2005) Zimmer, Inc. 4 sheets.
Birnbaum, Klaus, M.D., "Computer-Assisted Orthopedic Surgery With Individual Templates and Comparison to Conventional Method," SPINE vol. 26, No. 4, pp. 365-370 (2001) Lippincott Williams & Wilkins, Inc.
Botha, Charl P., Technical Report: DeVIDE—The Delft Visualisation and Image processing Development Environment, pp. 1-49 (May 31, 2006).
Cohen, Zohara A., et al. "Knee cartilage topography, thickness, and contact areas from MRI: in-vitro calibration and in-vivo measurements." Journal of the OsteoArthritis Research Society International. Osteoarthritis and Cartilage, (1999) vol. 7; No. 1 pp. 95-109.
Eckhoff, Donald G., et al., "Three-Dimensional Mechanics, Kinematics, and Morphology of the Knee Viewed in Virtual Reality," The Journal of Bone & Joint Surgery, vol. 81 (Dec. 4, 2005) pp. 71-80.
Fortin, Thomas, D.D.S., Ph.D., et al., "Precise Dental Implant Placement in Bone Using Surgical Guides in Conjunction with Medical Imaging Techniques," Journal of Oral Implantology, Clinical, vol. 26, No. 4 (2000) pp. 300-303.
Haaker, R.G., et al., "Minimal-invasive navigiert implantierte unikondyläre Knieendoprothese," Orthopäde 2006 35:1073-1079 (2006) Spinger Medizin Verlag.
Hafez, M.A., et al., "Computer-assisted Total Knee Arthroplasty Using Patient-specific Templating," Clinical Orthopaedics and Related Research, No. 444 (pp. 184-192) 2006 Lippincott Williams & Wilkins.
Hazen, Eric J., M.D., "Computer-Assisted Orthopaedic Sugery, A New Paradigm," Techniques in Orthopaedics® vol. 18, No. 2, (2003) pp. 221-229.
Hutmacher, Dietmar, W., "Scaffolds in tissue engineering bone and cartilage," Biomaterials, 2000 Elsevier Science Ltd. (pp. 2529-2543).
International Preliminary Report on Patentability and Written Opinion for PCT/US2009/039578 mailed Oct. 28, 2010 claiming benefit of U.S. Appl. No. 12/103,834, filed Apr. 16, 2008.
International Preliminary Report on Patentability and Written Opinion mailed Oct. 28, 2010 for PCT/US2009/039507 claiming benefit of U.S. Appl. No. 12/103,824, filed Apr. 16, 2008.
International Preliminary Report on Patentability for PCT/US2007/013223 mailed Dec. 24, 2008 claiming benefit of U.S. Appl. No. 11/756,057, filed May 31, 2007.
International Preliminary Report on Patentability mailed Mar. 31, 2011 for PCT/US2009/056670 claiming benefit of U.S. Appl. No. 12/211,407, filed Sep. 16, 2008.
International Search Report and Written Opinion for PCT/US2007/013223 mailed Nov. 26, 2007, claiming benefit of U.S. Appl. No. 11/756,057, filed May 31, 2007.
International Search Report and Written Opinion for PCT/US2009/039507 mailed Jul. 14, 2009, claiming benefit of U.S. Appl. No. 12/103,824.

International Search Report and Written Opinion for PCT/US2009/056670 mailed Mar. 2, 2010 claiming benefit of U.S. Appl. No. 12/211,407, filed Sep. 16, 2008.

International Search Report and Written Opinion mailed Apr. 22, 2010 for PCT/US2010/024579 claiming benefit of U.S. Appl. No. 12/389,930, filed Feb. 20, 2009.

International Search Report and Written Opinion mailed Aug. 19, 2010 for PCT/US2010/024584 claiming benefit of U.S. Appl. No. 12/389,901, filed Feb. 20, 2009.

International Search Report and Written Opinion mailed Dec. 7, 2010 for PCT/US2010/050701 claiming benefit of U.S. Appl. No. 12/571,969, filed Oct. 1, 2009.

International Search Report and Written Opinion mailed Jul. 31, 2009 for PCT/US2009/039578 claiming benefit of U.S. Appl. No. 12/103,834, filed Apr. 16, 2008.

International Search Report and Written Opinion mailed Jun. 10, 2010 for PCT/US2010/038177 claiming benefit of U.S. Appl. No. 12/483,807, filed Jun. 12, 2009.

International Search Report and Written Opinion mailed Jun. 4, 2010 for PCT/US2010/024073 filed Feb. 12, 2010, claiming benefit of U.S. Appl. No. 12/371,096, filed Feb. 13, 2009.

International Search Report and Written Opinion mailed May 9, 2011 for PCT/US2011/026412 claiming benefit of U.S. Appl. No. 12/872,663, filed Aug. 31, 2010.

International Search Report and Written Opinion mailed Oct. 5, 2010 for PCT/US2010/038845 claiming benefit of U.S. Appl. No. 12/486,992, filed Jun. 18, 2009.

Invitation to Pay Additional Fees mailed May 3, 2011 for PCT/US2011/026333 claiming benefit of U.S. Appl. No. 12/714,023, filed Feb. 26, 2010.

Invitation to Pay Additional Fees with Partial International Search mailed Nov. 26, 2009 for PCT/US2009/056670.

Kaus, Michael R., Ph.D., "Automated Segmentation of MR Images of Brain Tumors," Radiology, vol. 218, No. 2, (2001) pp. 586-591.

Kelly, Todd C., M.D., "Role of Navigation in Total Hip Arthroplasty," The Journal of Bone & Joint Surgery(2009) pp. 153-158. vol. 91-A, Supplement 1.

Klein, M., "Robot assisted insertion of craniofacial implants—clinical experience," CARS 2001, pp. 133-138 (2001) Elsevier Science B.V.

Lombardi, Adolph, et al., "Patient-Specific Approach in Total Knee Arthroplasty," Knee Orthopedics, ORTHOSuperSite (Sep. 1, 2008), 5 pages, http://www.orthosupersite.com/view.aspx?rid=31419, printed May 20, 2010.

Lynch, John A., et al., "Cartilage segmentation of 3D MRI scans of the osteoarthritic knee combining user knowledge and active contours," Medical Imaging 2000: Image Processing SPIE vol. 3979 (2000) pp. 925-935.

Murphy, S.B., et al. "The Hip Sextant: Navigation of Acetabular Component Orientation Using a Mechanical Instrument," brochure. (2009) 1 page.

Nicholls, Paul, M.D., "Trauma Grand Rounds PMI (Patient-Matched Implants)" brochure, Biomet Orthopedics, Inc., (Feb. 29, 2000) 1 page.

Overhoff, H.M., et al., "Total Knee Arthroplasty: Coordinate System Definition and Planning based on 3-D Ultrasound Image Volumes," CARS 2001, pp. 283-288, (2001) Elsevier Science B.V.

Portheine, F., "CT-basierte Planung und DISOS-Schablonennavigation in der Kniegelenkendoprothetik," in Navigation und Robotic in der Gelenk—und Wirbelsäulenchirugie, Kapitel 32, Springer Verlag (2003) pp. 262-269.

Portheine, F., et al., Entwicklung eines klinischen Demonstrators für die computerunterstützte Orthopädische Chirurgie mit CT-Bildbasierten Individualschablonen, Bildverarbeitung fur die Medizin (1998) 5 pages.

Portheine, K., "Development of a clinical demonstrator for computer assisted orthopedic surgery with CT-image based individual templates," Computer Assisted Radiology and Surgery, pp. 944-949, (1997) Elsevier Science B.V.

Radermacher, "Computer Assisted Orthopaedic Surgery with Image Based Individual Templates," Clinical Orthopaedics and Related Research No. 354, pp. 28-38 (1998) Lippincott Williams & Wilkins.

Radermacher, K., et al., "Computer Integrated Orthopaedic Surgery: Connection of Planning and Execution in Surgical Intervention," Computer-integrated surgery: technology and clinical applications, (1996) pp. 451-463.

Radermacher, K., et al., "CT Image-Based Planning and Execution of Interventions in Orthopedic Surgery Using Individual Templates, Experimental Results and Aspects of Clinical Applications," Computer Assisted Orthopedic Surgery (CAOS), pp. 42-52, (1995) Hogrefe & Huber Publishers.

Radermacher, K., et al., "Image Guided Orthopedic Surgery Using Individual Templates," Springer Berlin/Heidelberg, CVRMed-MRCAS'97, vol. 1205/1997 pp. 606-615).

Radermacher, K., et al., "Technique for Better Execution of CT Scan Planned Orthopedic Surgery on Bone Structures," Supplied by the British Library—"The world's knowledge" 2nd Congress of ISCAS Conference in Berlin Germany (Jun. 1995) pp. 933-938.

Radermacher, Klaus, et al. "Computer Assisted Orthopaedic Individual Templates." Clinical Orthopaedics and Related Research. (Sep. 1998) No. 354; pp. 28-38.

Schuller-Götzburg, P., et al., 3D-Implantatplanung und Stereolithographie-Implantatbohrschablonen, Stomatologie 101.3, pp. 55-59 (2004).

Sharp, S. Michael, Ph.D., Patient-Specific, Resurfacing Bi-Compartmental Arthuroplasty, Futuretech, Orthopaedic Product News (Mar./Apr. 2008) pp. 12-15.

Sisto, Domenick, J., et al., "Custom Patellofemoral Arthroplasty of the Knee Surgical Technique," Journal of Bone and Joint Surgery, vol. 89-A, pp. 214-225 (2007).

Slammin, John et al, "Do You Have This Implant in My Size?", MDT Medical Design Technology, 3 pages, http://www.mdtmag.com/scripts/ShowPR.asp?PUBCODE=046&ACCT=0007796&ISSUE . . . accessed Jul. 31, 2008.

Steinwachs, Matthias Reinhard, "Cartilage Repair—Autologous Chondrocyte Transplantation and Autologous Matrix-induced Chondrogenesis," European Musculoskeletal Review (2006) pp. 65-68.

International Preliminary Report on Patentability for PCT/US2010/050701 mailed Apr. 12, 2012 claiming benefit of U.S. Appl. No. 12/571,969, filed Oct. 1, 2009.

International Search Report and Written Opinion mailed Mar. 5, 2012 for PCT/US2011/057300 claiming benefit of U.S. Appl. No. 12/938,905, filed Nov. 3, 2010.

International Search Report and Written Opinion mailed May 8, 2012 for PCT/US2012/026356 claiming benefit of U.S. Appl. No. 13/041,883, filed Mar. 7, 2011.

Thoma, W., et al., "Endoprothetischen Versorgung des Kniegelenks auf der Basis eines 3D-computertomographischen Subtraktionversfahrens," Zuma Thema: Computergestützte orthopädische Chirugie, Der Orthopäde 29:641-644 Springer-Verlag (Jul. 2000) Translation provided: Thoma, W., "Endoprosthetic care of the knee joint based on a 3D computer chromatography subtraction process," Topic: Computer-aided orthopedic surgery. Orthopedist 2000 29:641-644 Springer Verlag (Jul. 2000).

International Preliminary Report on Patentability and Written Opinion mailed Sep. 7, 2012 for PCT/US2011/026333 claiming benefit of U.S. Appl. No. 12/714,023, filed Feb. 26, 2010.

* cited by examiner

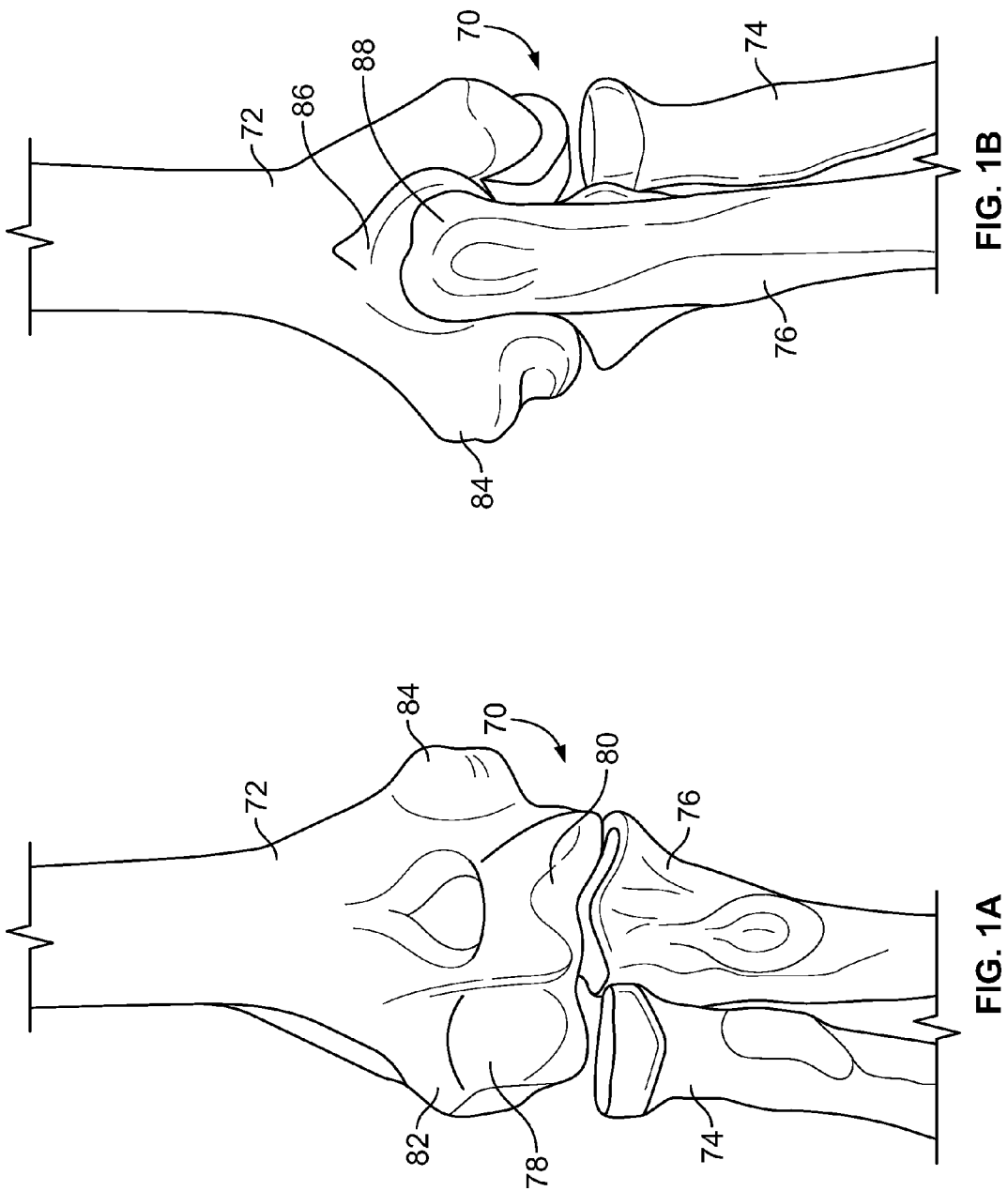

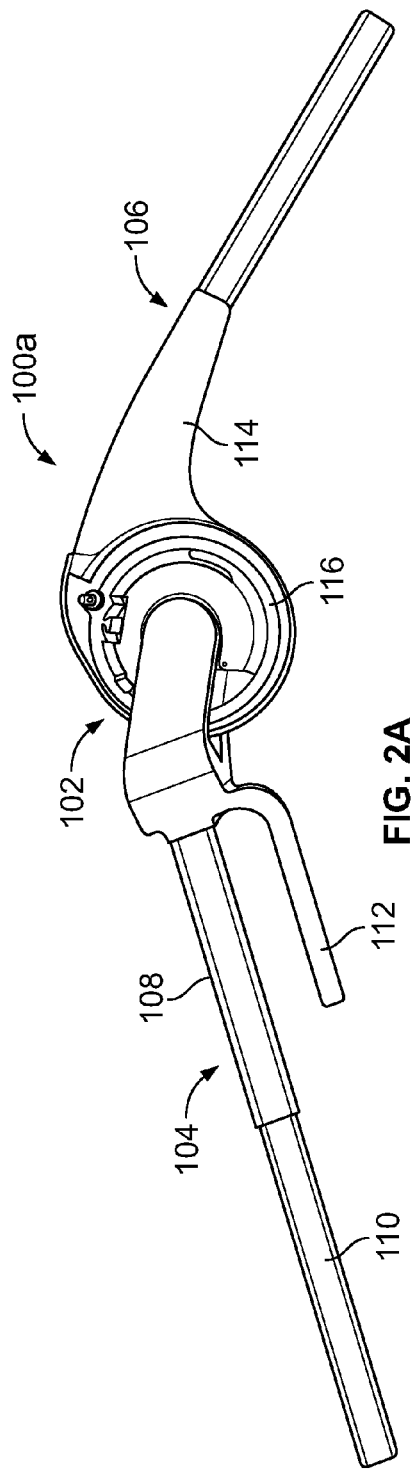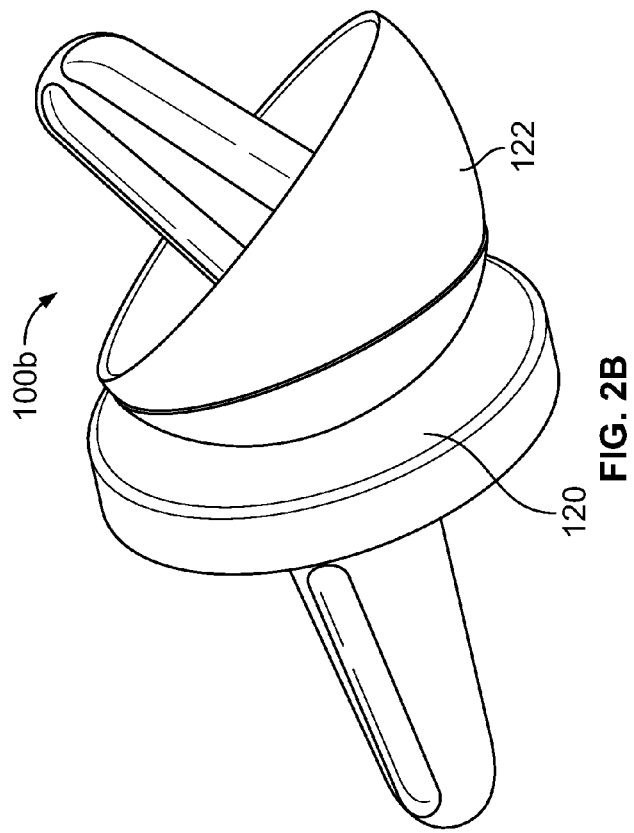
FIG. 2A
FIG. 2B

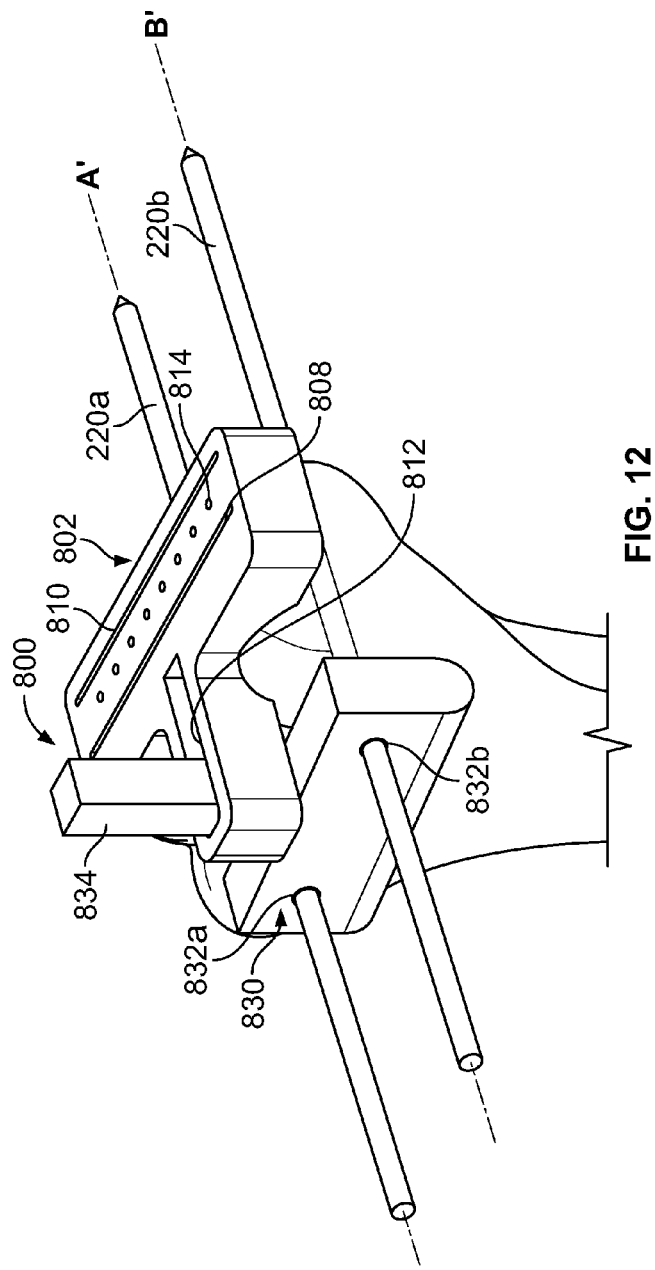
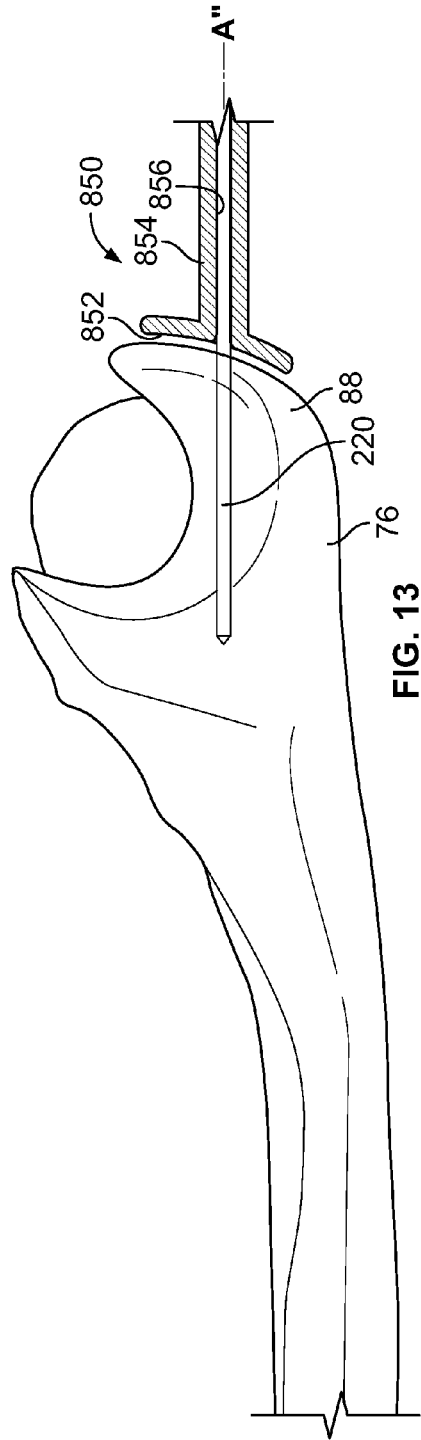
FIG. 12
FIG. 13

PATIENT-SPECIFIC ELBOW GUIDES AND ASSOCIATED METHODS

CROSS-REFERENCE TO RELATED APPLICATIONS

This application is a continuation-in-part of U.S. application Ser. No. 12/714,023, filed Feb. 26, 2010, which is a continuation-in-part of U.S. application Ser. No. 12/571,969, filed Oct. 1, 2009, which is a continuation-in-part of U.S. application Ser. No. 12/389,901, filed Feb. 20, 2009, which is a continuation-in-part of U.S. application Ser. No. 12/211,407, filed Sep. 16, 2008, which is a continuation-in-part of U.S. application Ser. No. 12/039,849, filed Feb. 29, 2008, which: (1) claims the benefit of U.S. Provisional Application No. 60/953,620, filed on Aug. 2, 2007, U.S. Provisional Application No. 60/947,813, filed on Jul. 3, 2007, U.S. Provisional Application No. 60/911,297, filed on Apr. 12, 2007, and U.S. Provisional Application No. 60/892,349, filed on Mar. 1, 2007; (2) is a continuation-in-part U.S. application Ser. No. 11/756,057, filed on May 31, 2007, which claims the benefit of U.S. Provisional Application No. 60/812,694, filed on Jun. 9, 2006; (3) is a continuation-in-part of U.S. application Ser. No. 11/971,390, filed on Jan. 9, 2008, which is a continuation-in-part of U.S. application Ser. No. 11/363,548, filed on Feb. 27, 2006; and (4) is a continuation-in-part of U.S. application Ser. No. 12/025,414, filed on Feb. 4, 2008, which claims the benefit of U.S. Provisional Application No. 60/953,637, filed on Aug.

This application is continuation-in-part of U.S. application Ser. No. 12/872,663, filed on Aug. 31, 2010, which claims the benefit of U.S. Provisional Application No. 61/310,752 filed on Mar. 5, 2010.

This application is also a continuation-in-part of U.S. application Ser. No. 12/483,807, filed on Jun. 12, 2009, which is a continuation-in-part of U.S. application Ser. No. 12/371,096, filed on Feb. 13, 2009, which is a continuation-in-part of U.S. application Ser. No. 12/103,824, filed on Apr. 16, 2008, which claims the benefit of U.S. Provisional Application No. 60/912,178, filed on Apr. 17, 2007.

The disclosures of the above applications are incorporated herein by reference.

INTRODUCTION

Various patient specific templates and other guides are used for knee arthroplasty. The present teachings provide various patient-specific alignment guides, cutting guides and other instruments for the elbow joint.

SUMMARY

The present teachings provide a patient-specific alignment guide that includes a three-dimensional engagement surface customized in a pre-operating planning stage by computer imaging to closely mate and conform to a corresponding bone portion of a patient's elbow joint.

In one embodiment, the patient-specific-alignment guide defines a first longitudinal guiding bore aligned with a reference axis associated with the elbow joint of patient when the alignment guide is mounted onto the corresponding bone portion.

In another embodiment, the patient-specific-alignment guide defines a guiding bore for guiding a pin along a reference axis and a guiding surface for guiding a blade for a bone-cut along a patient-specific resection plane, wherein the guiding bore and guiding surface are customized for the patient during a preoperative planning stage.

The present teachings provide a method of preparing an elbow joint for an implant. In one embodiment, the method includes mounting a patient-specific alignment guide including a three-dimensional engagement surface custom-made by computer imaging to a corresponding closely conforming bone portion of a patient's elbow joint, and inserting into the bone portion a first pin along an anatomic axis of the elbow joint through a first longitudinal guiding bore of the patient-specific alignment guide. The method also includes inserting into the bone portion a second pin through a second longitudinal guiding bore of the patient-specific alignment guide, and removing the patient-specific alignment guide without removing the first and second pins. The method further includes slidably mounting a first resection guide over the first and second pins, and resecting the bone portion for receiving an implant.

In another embodiment, the method includes mounting a patient-specific alignment guide including a three-dimensional engagement surface custom-made by computer imaging to a corresponding closely conforming bone portion of a patient's elbow joint. The method also includes inserting into the bone portion a first pin along an anatomic axis of the elbow joint through a first longitudinal guiding bore of the patient-specific alignment guide, and resecting the bone portion along a first plane through a first longitudinal slot of the patient-specific alignment guide for receiving an implant.

The present teachings provide a medical device for an elbow joint including a cutting component and a guiding component. The cutting component includes a planar engagement surface for engaging or contacting a planar resected surface of a bone, a first elongated slot along a first plane perpendicular to the engagement surface for guiding a first planar resection and a second elongated slot along a second plane at an oblique angle relative the first plane for guiding a second planar resection at an oblique angle relative to the first planar resection. The cutting component also includes an aperture. The guiding component includes first and second longitudinal bores aligned along first and second reference axes for receiving first and second alignment pins engageable with the bone. The guiding component includes an extension slidably received through the aperture of the cutting component for orienting the first and second planes of the cutting component in pre-planned orientations relative to the first and second reference axes.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein:

FIG. 1A is an anterior view illustrating the bones of a right elbow;

FIG. 1B is a posterior view illustrating the bones of a right elbow;

FIG. 2A is a perspective view of the Discovery® Elbow System for total elbow joint replacement commercially available from Biomet Orthopedics, Inc., Warsaw, Ind., USA;

FIG. 2B is a perspective view of a Lateral Resurfacing Elbow (LRE™) system commercially available from Biomet UK, Ltd, Bridgend, South Wales, UK;

FIG. 12 is an environmental perspective view of a cutting guide supported on first and second posterior pins for performing an anterior cut and an angled posterior cut according to the present teachings;

FIG. 13 is an environmental sectional view of a patient-specific guide illustrated for the ulna of an elbow joint according to the present teachings;

DESCRIPTION OF VARIOUS ASPECTS

Figure 3:
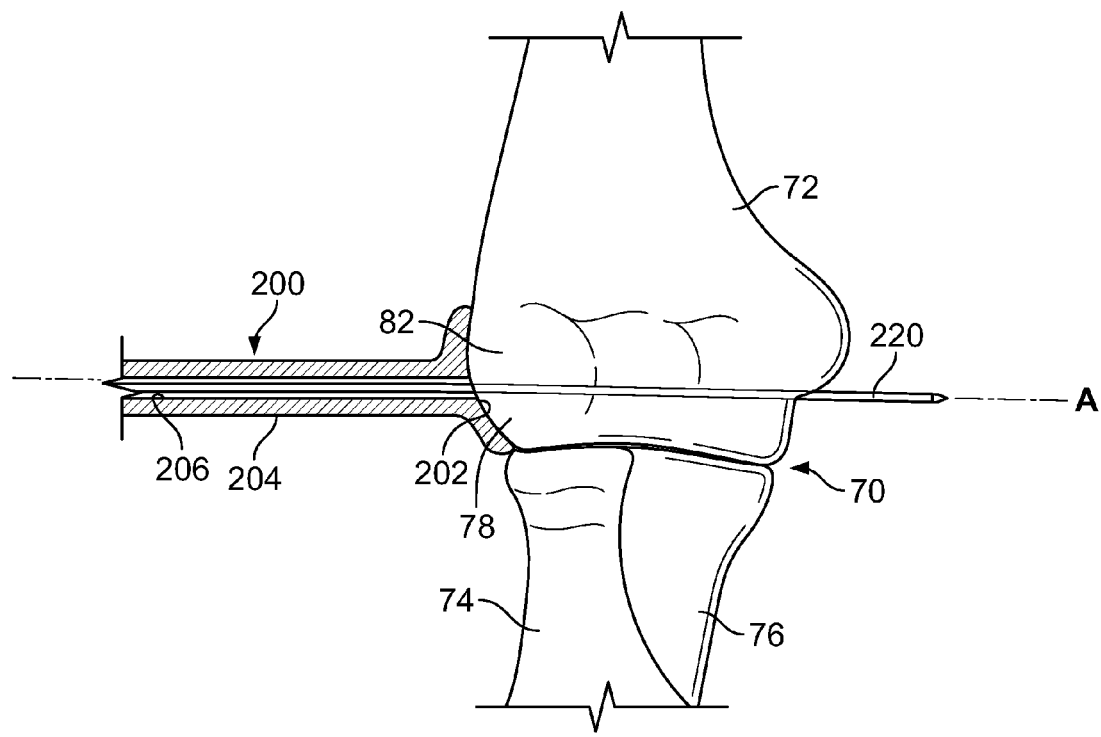
FIG. 3 is an environmental perspective view of a patient-specific alignment guide illustrated for the distal humerus according to the present teachings.

The present teachings generally provide patient-specific surgical instruments that include, for example, alignment guides, drill guides, templates, cutting/resection guides for use in elbow joint replacement, elbow resurfacing procedures and other procedures related to the elbow joint or the various bones of the elbow joint. The patient-specific instruments can be used either with conventional implant components or with patient-specific implant components prepared with computer-assisted image methods. Computer modeling for obtaining three dimensional images of the patient's anatomy using MRI or CT scans of the patient's anatomy, the patient specific prosthesis components, and the patient-specific guides, templates and other instruments can be provided by various CAD programs and/or software available, for example, by Materialise USA, Ann Arbor, Mich.

The patient-specific instruments and associated patient-specific implants disclosed herein can be generally formed using computer modeling based on the patient's 3-D anatomic image generated from image scans. The patient-specific instruments can have a three-dimensional engagement surface that is made to conformingly contact and match a three-dimensional image of the patient's bone surface (imaged selectively with associated soft tissues or without soft tissue, i.e. an actual bone surface), by the computer methods discussed above. The patient-specific instruments can include custom-made guiding formations, such as, for example, guiding bores or cannulated guiding posts or cannulated guiding extensions or receptacles that can be used for supporting or guiding other instruments, such as drill guides, reamers, cutters, cutting guides and cutting blocks or for inserting pins or other fasteners according to a surgeon-approved pre-operative plan.

In various embodiments, the patient-specific instruments can also include one or more patient-specific cutting guides for receiving and guiding a cutting blade at corresponding patient-specific resection orientations relative to a selected anatomic axis for the specific patient. The patient-specific instruments can also include guiding formations for guiding the implantation of patient-specific or off-the-shelf implants associated with the surgical procedure, such as humeral and ulnar implant components. The geometry, shape and orientation of the various features of the patient-specific instruments, as well as various patient-specific implants, if used, can be determined during the pre-operative planning stage of the procedure in connection with the computer-assisted modeling of the patient's anatomy. During the pre-operative planning stage, patient-specific instruments, custom, semi-custom or non custom implants and other non custom tools, can be selected and the patient-specific components can be manufactured for a specific-patient with input from a surgeon or other professional associated with the surgical procedure, as described in the commonly assigned and co-pending patent applications listed in the cross reference section and incorporated herein by reference.

In the following discussion, the terms "patient-specific", "custom-made" or "customized" are defined to apply to components, including tools, implants, portions or combinations thereof, which include certain geometric features, including surfaces, curves, or other lines, and which are made to closely conform as mirror-images or negatives of corresponding geometric features of a patient's anatomy obtained or gathered during a pre-operative planning stage based on 3-D computer images of the corresponding anatomy reconstructed from image scans of the patient by computer imaging methods. Further, patient specific guiding features, such as, guiding apertures, guiding slots, guiding members or other holes or openings that are included in alignment guides, drill guides, cutting guides, rasps or other instruments or in implants are defined as features that are made to have positions, orientations, dimensions, shapes and/or define cutting planes and axes specific to the particular patient's anatomy including various anatomic or mechanical axes based on the computer-assisted pre-operative plan associated with the patient.

Referring to FIGS. 1A and 1B, anterior and posterior views of an elbow joint 70 are illustrated to highlight areas on which the patient-specific guides of the present teachings are adapted to conform to. The elbow joint 70, including subchondral bone with or without cartilage or other soft tissue depending on surgeon requirements/recommendation of a particular patient, is modeled preoperatively as three-dimensional computer image from a series of scans of the elbow joint 70 of a particular patient. As illustrated schematically for simplicity and without showing any soft tissue for further reference below, the elbow joint 70 includes the bone portions of the distal humerus 72, the proximal radius 74 and the proximal ulna 76. In the anterior view of FIG. 1A, the capitellum (capitulum humeri) is illustrated at 78, the trochlea at 80, and the lateral and medial epicondyles at 82, 84 respectively. In the posterior view of FIG. 1B, the olecranon fossa of the distal humerus 72 is illustrated at 86 and the olecranon of the proximal ulna is illustrated at 88.

Referring to FIGS. 2A and 2B, exemplary implants 100a, 100b for the elbow joint are illustrated. FIG. 2A illustrates an exemplary total elbow arthroplasty implant 100a, commercially available from Biomet Orthopedics, Inc., Warsaw, Ind., USA, as Discovery® Elbow System. The elbow arthroplasty implant 100a includes a spherical hinge 102 coupling a humeral component 104 and an ulnar component 106. The humeral component 104 includes a bowed stem 108, a cylindrical base 110 and an anti-rotation flange 112. The ulnar component 106 includes a stem 114 forming an anatomic anterior neck angle and a polyethylene insert 116.

FIG. 2B illustrates an exemplary elbow resurfacing implant 100b commercially available from Biomet UK, Ltd, Bridgend, South Wales, UK, as Lateral Resurfacing Elbow (LRE™) system. This implant 100b is modular and includes a radial head component 120 and a capitellar component 122 with optional implantation of one or both components. Details of the implantation techniques and surgical procedures for the implants are available in the manufacturers' websites.

Referring to FIG. 3, a patient-specific alignment guide 200 is illustrated. The patient-specific alignment guide 200 can be specific to portions of the lateral epicondyle 82 and/or capitellum 78 of the distal humerus 72 of the patient and includes a three-dimensional engagement surface 202, custom-made by computer imaging to conform to a corresponding portion of a patient's corresponding anatomy, such an area of the epicondyle or capitellum or other area of the distal humerus 72. The alignment guide 200 can include a patient-specific guiding feature 204, which can be computer modeled to be aligned with a reference axis, including an axis of rotation A of the elbow joint 70 of the patient. The guiding feature 204 can be a tubular or partially tubular structure with an elongated guiding bore 206 at a patient-specific orientation and location for guiding a drill bit, a pin, or other tool to make a hole through the distal humerus 72 at the reference axis A. A guiding/alignment pin 220, such as a Steinmann pin, can be inserted into the distal humerus 72 through the guiding bore 206 when the alignment guide 200 is mounted on the distal humerus 72. It should be noted that because of the patient-specific nature of the engagement surface 202, the alignment guide 200 can fit in a unique position/orientation over the capitellum 78. In some embodiments, the alignment guide 200 can automatically align the guiding bore 206 along the reference axis A, which can also be an axis of rotation of the patient's elbow joint or any other axis.

Figure 4A:
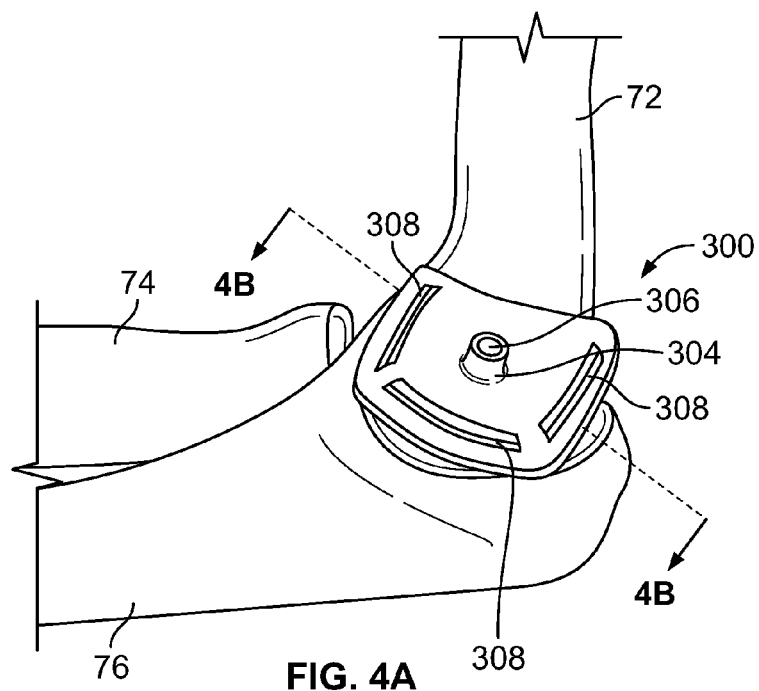
FIG. 4A is an environmental perspective view of a patient-specific guide illustrated for the distal humerus according to the present teachings.
Figure 4B:
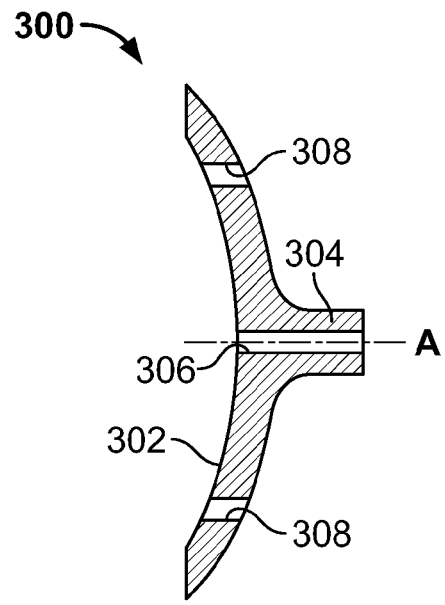
FIG. 4B is a sectional of the patient-specific guide of FIG. 4A taken along line 4B-4B.
Figure 4C:
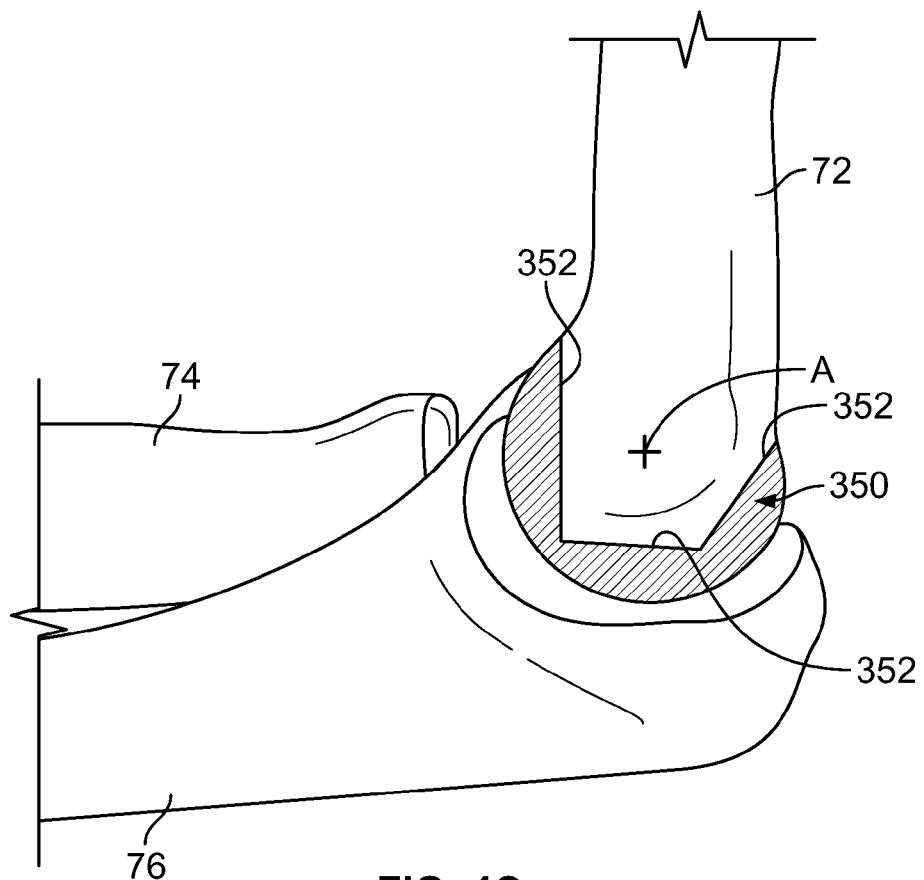
FIG. 4C is an environmental sectional view of an implant fitted to a resected elbow joint.

Referring to FIGS. 4A and 4B, a patient-specific combined alignment and resection/cutting guide 300 for the distal humerus is illustrated. The combined guide 300 includes a three-dimensional patient-specific engagement surface 302, a tubular guiding feature 304 with an internal guiding bore 306 at a patient-specific orientation and location for a pin and a plurality of elongated guiding slots 308 for guiding a blade to perform the cuts required for inserting an elbow implant. In some embodiments, the guiding bore 306 can reference a selected anatomic axis of the joint or any other axis. Three exemplary guiding slots 308 for distal, anterior and posterior humeral cuts are shown. It should be noted that any number of desired guiding slots 308 may be included in the guide 300. An exemplary humeral implant 350, having inner surfaces 352 corresponding to distal, anterior and posterior humeral cuts, is shown in FIG. 4C.

Figure 5:
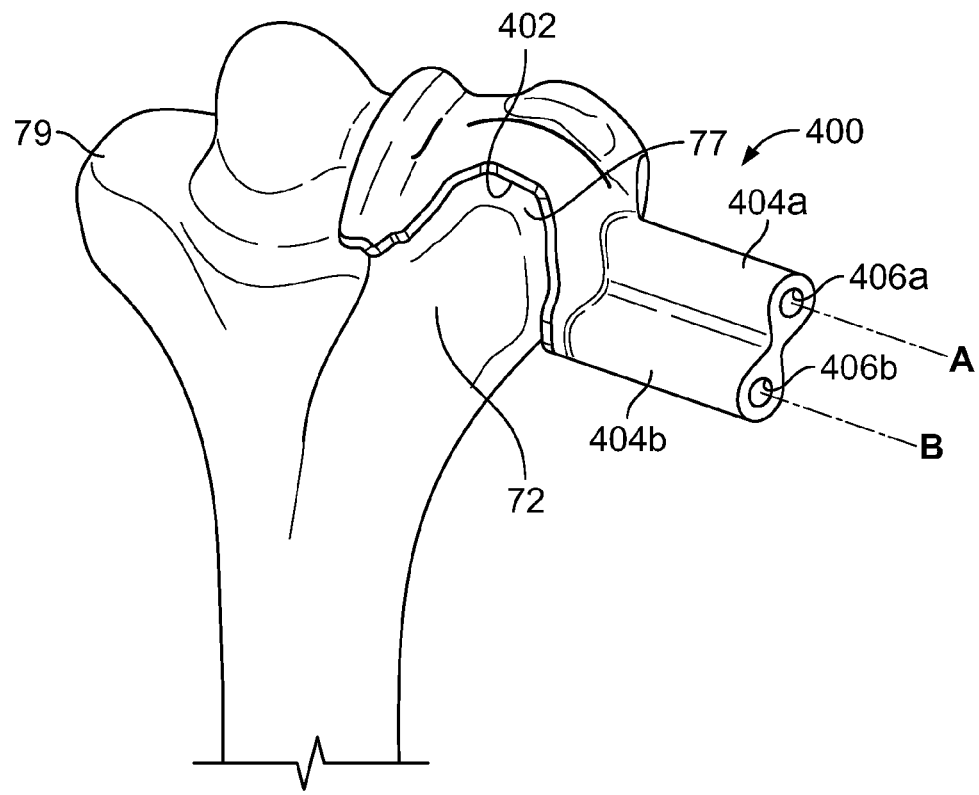
FIG. 5 is an environmental perspective view of a patient-specific alignment guide illustrated for the distal humerus according to the present teachings.
Figure 6:
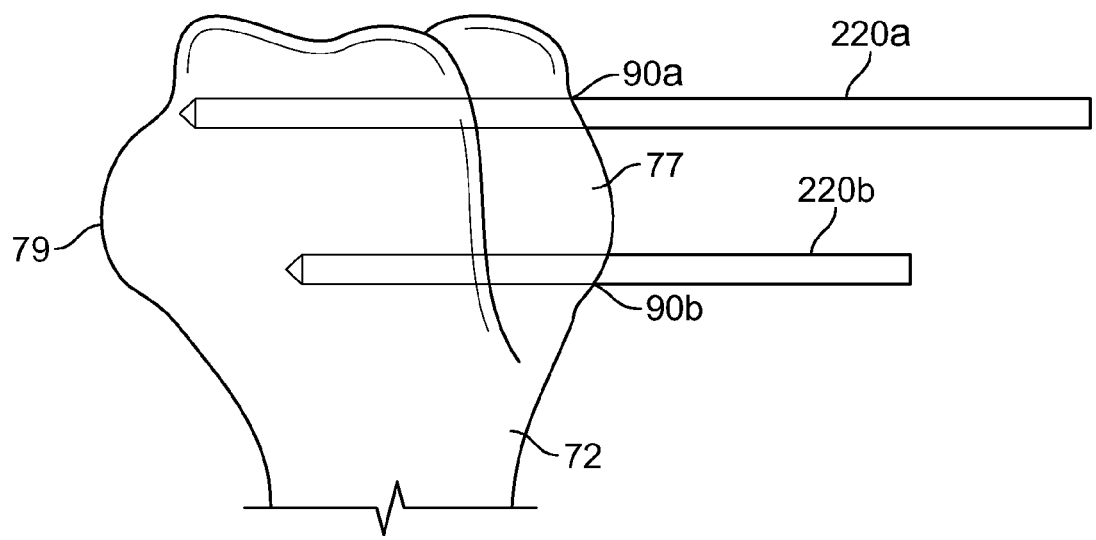
FIG. 6 an environmental sectional view of placement of first and second pins in locations determined by a patient-specific guide according to the present teachings.

Referring to FIGS. 5 and 6, a patient-specific alignment guide 400 for the lateral surface 77 of the distal humerus 72 is illustrated. The alignment guide 400 includes a three-dimensional patient-specific engagement surface 402 for the lateral surface 77 of the distal humerus 72, optionally including portions of the lateral epicondyle or the capitellum or other anatomic landmarks of the lateral surface 77. The alignment guide 400 can also include a first guiding feature 404a with a first internal guiding bore 406a at a patient-specific orientation and location for a first alignment pin 220a. As discussed above, in some embodiments the guiding bore 406a can reference an anatomic axis (or first axis) A, such as an epicondylar axis or a rotation axis of the elbow joint of the specific patient, or any other selected axis. The alignment guide 400 can include a second guiding feature 404b with a second internal guiding bore 406b for a second alignment pin 220b referencing a second axis B parallel to the first axis A. The second alignment pin 220b can be provided for additional rotational stability and for supporting various resection instruments, as discussed below. The corresponding first and second alignment pins 220a, 220b extend from the lateral surface 77 toward the medial surface 79 of the distal humerus 72 and can be used for guiding osteotomy instruments or other instruments along patient specific orientations and locations of the axes A and B, as discussed below. The first and second guiding features 404a, 404b can be formed as a single integral (monolithic) structure as shown in FIG. 5, or as two separate elongated structures extending from the alignment guide 400.

After the first and second alignment pins 220a, 220b are fixed on the lateral surface 77 of the distal humerus 72, the alignment guide 400 is slid off the first and second alignment pins 220a, 220b and removed, while the first and second alignment pins 220a, 220b remain attached to the distal humerus, as illustrated in FIG. 6. Alternatively, first and second holes 90a, 90b can be drilled or marked through the first and second guiding bores 406a, 406b for the first and second alignment pins 220a, 220b, the alignment guide 400 removed, and then the first and second alignment pins 220a, 220b inserted through the pre-drilled or pre-marked holes 90a, 90b.

Figure 7A:
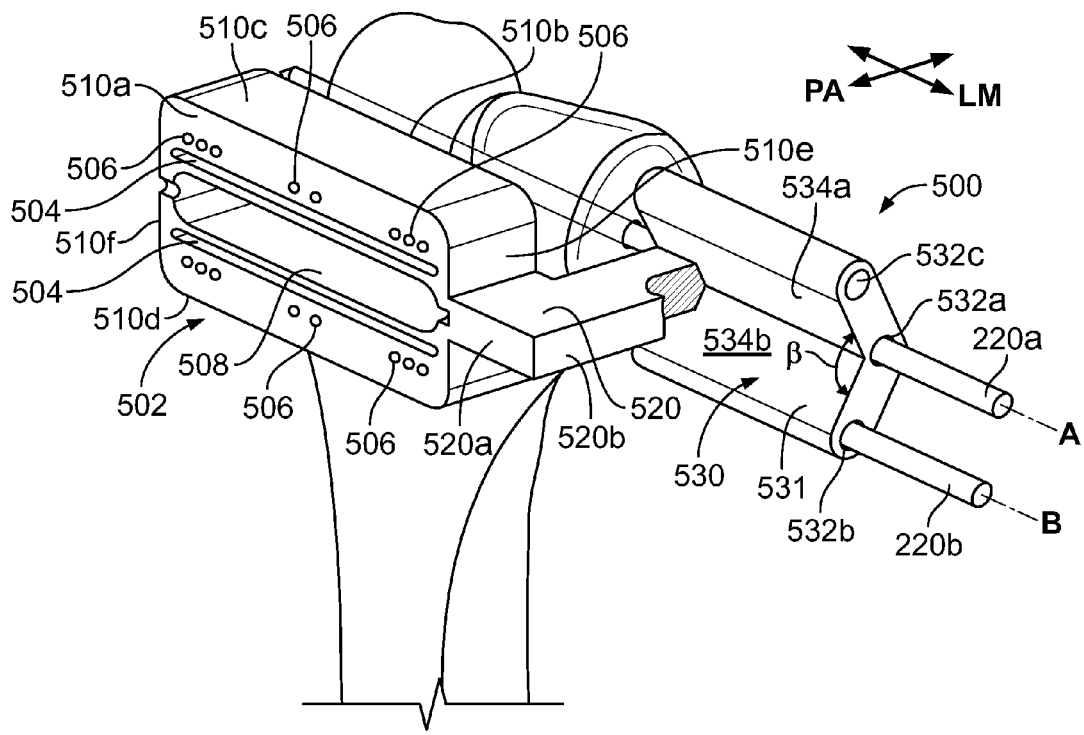
FIGS. 7A and 7B are environmental perspective views illustrating a cutting guide supported on first and second lateral pins for performing a distal cut according to the present teachings.
Figure 7B:
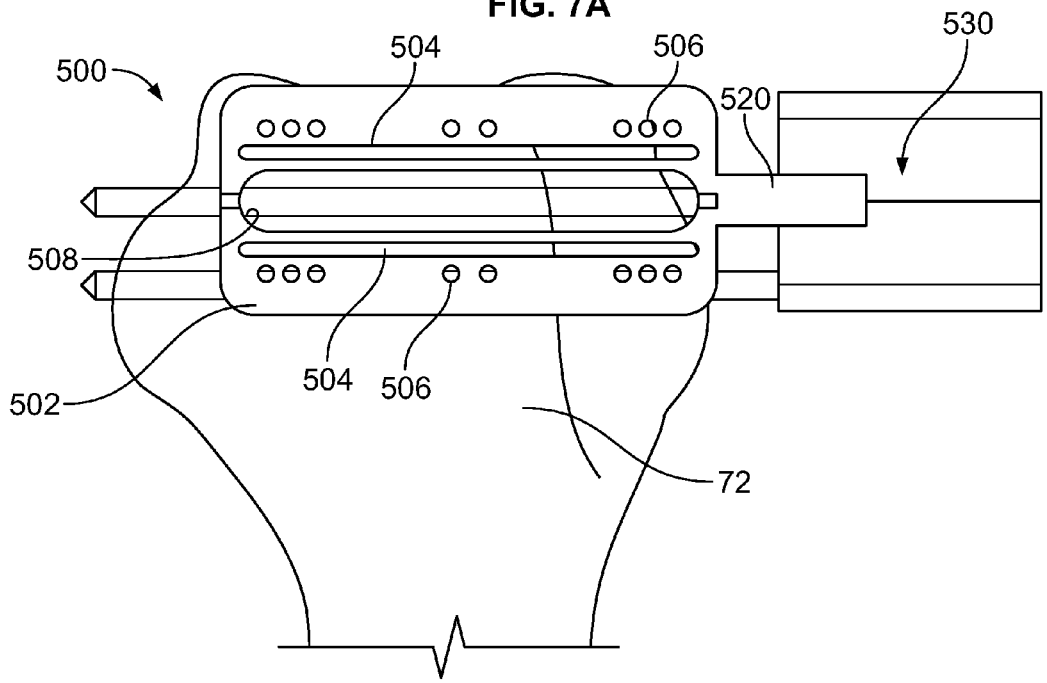

Referring to FIGS. 7A and 7B, a posterior resection or cutting guide 500 can be mounted on and aligned by the first and second alignment pins 220a, 220b for performing a distal cut of the distal humerus from a posterior to an anterior surface of the distal humerus. The posterior cutting guide 500 can include a cutting component 502 oriented to abut against the posterior surface of the distal humerus and a guiding component 530 oriented for lateral placement relative to the distal humerus and slidably mounted over the first and second alignment pins 220a, 220b, as illustrated in FIG. 7A. The lateral-medial orientation is illustrated with an arrow LM and the posterior-anterior orientation is illustrated with arrow PA in FIG. 7A. The cutting and guiding components 502, 530 can be modularly or integrally connected via a connector 520, as discussed below.

The cutting component 502 can be in the form of a cutting block having opposite first and second (front and back/engagement) surfaces 520a, 510b, opposite side surfaces (distal and proximal) 510c, 510d, and opposite end surfaces (lateral and medial) 510e, 510f. The cutting component 502 can include one or more elongated slots 504 extending along the lateral-medial orientation for receiving a saw blade. The elongated slots 504 are automatically aligned along patient-specific positions determined during the preoperative planning stage for the patient when the posterior cutting guide 500 is mounted over the first and second alignment pins 220a, 220b. The cutting component 502 can also include a window elongated in the lateral-medial direction. The cutting component 502 can include a plurality of holes 506 that can be arranged in clusters for locking the cutting guide 500 with pins onto the distal humerus during the cutting operation.

The guiding component 530 can include a body 531 having first and second longitudinal guiding bores 532a, 532b slidably mounted over the first and second alignment pins 220a, 220b to orient the cutting component 502 in a patient-specific orientation and position for performing the distal cut as determined in the preoperative planning stage. Although the body 531 of the guiding component 530 can have any shape, such as a cylindrical or prismatic bar, some shapes allow the posterior cutting guide 500 to be used in both the right and left humerus without increasing the bulk or size of the components. An exemplary shape of the body 531 for right and left humerus is illustrated in FIG. 7A and includes first and second portions 534a, 543b coupled at an angle β defining a body 501 with an arrow-shaped cross-section. The first guiding bore 532a for the anatomic axis A is positioned at the juncture of the first and second portions 534a, 534b (apex of the angle β). The second guiding bore 534b is defined through the second portion 534b and a third guiding bore 532c is defined through the first portion 534a symmetrically to the second guiding bore 532b. The first and second guiding bores 532a, 532b can, thus, be used for the left humerus, while the first and third guiding bore 532a, 532c can be used for the right humerus in connection with the cutting component 502 which is symmetric about a medial-lateral axis, as illustrated in FIG. 2A.

As discussed above, the connector 520 can be integrally attached to the cutting and guiding components 502, 530, as illustrated in FIG. 7A. The connector 520 can be a polygonal bar for providing a clearance between the cutting and guiding components 502, 530. For example, the connector 520 can be L-shaped with a first end portion 520a coupled to cutting component 502 and a second end portion 520b coupled to the guiding component 530. Intermediate portions may be included for certain attachment configurations. The first end portion 520a can be attached to any of the surfaces 510e, 510c, 510d.

Figure 7C:
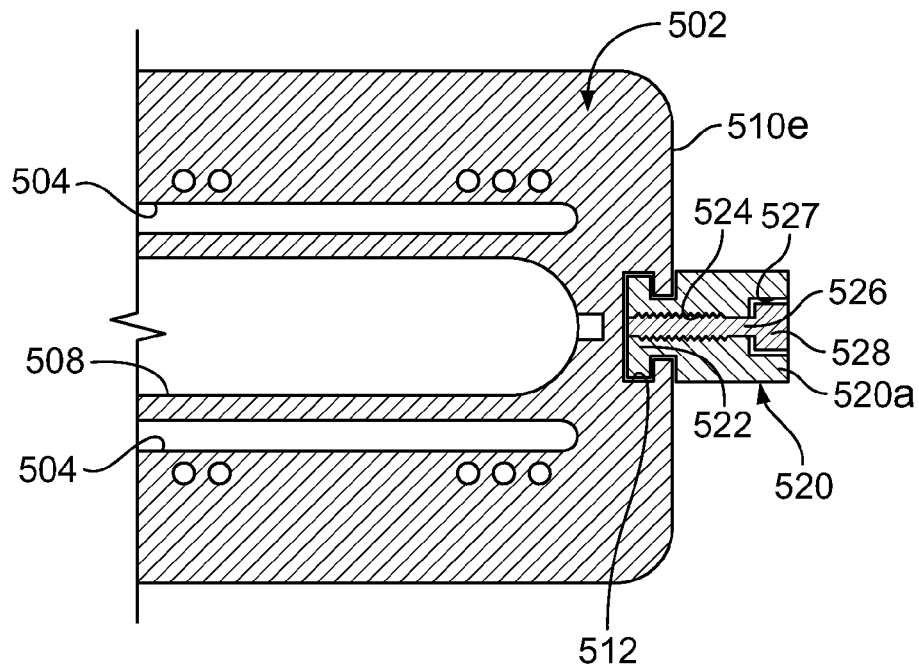
FIG. 7C is a detail of a modular posterior cutting guide for performing a distal cut according to the present teachings.
Figure 7D:
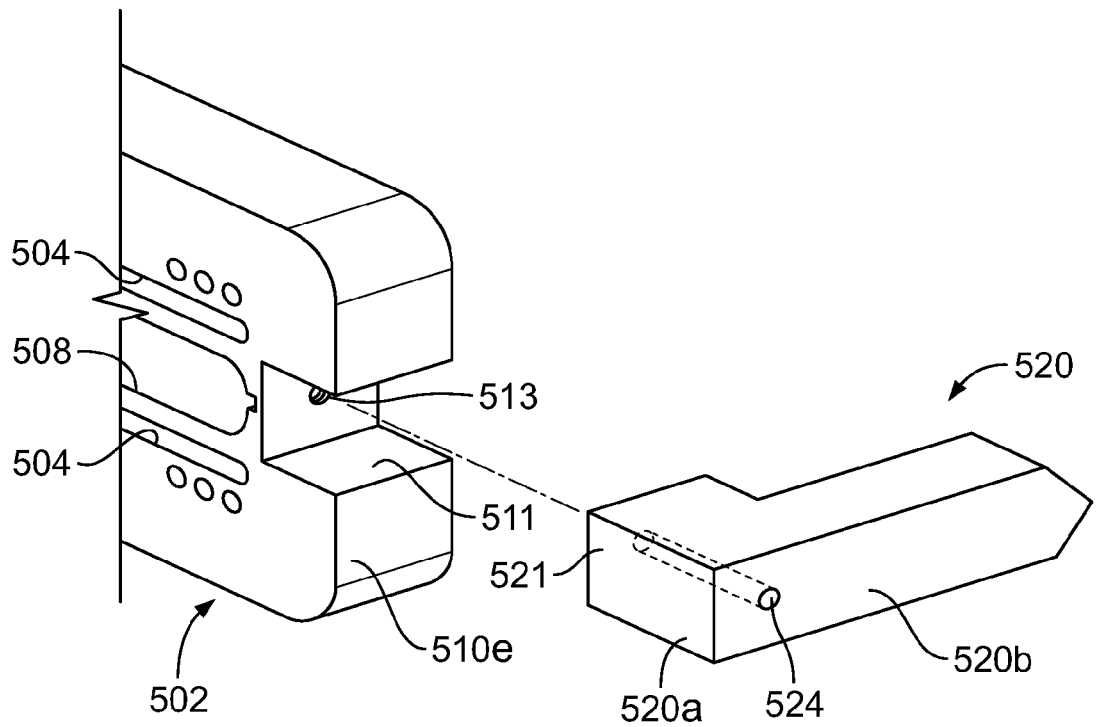
FIG. 7D is a detail of a modular posterior cutting guide for performing a distal cut according to the present teachings.

The connector 520 can also be removably coupled to the cutting component 502, as illustrated in FIGS. 7C and 7D. In one exemplary embodiment, the first end portion 520a of the connector can be removably coupled to one of the side or end surfaces 510e, 510f, 510c, 510d of the cutting component with T-slot or dovetail or rectangular slot or other quick connect/disconnect connection. FIG. 7C illustrates a T-slot connection at the lateral end surface 510e of the cutting component 502. A split T-shaped extension 522 of the first end portion 520a can be slidably received in a corresponding T-shaped slot 512 defined on lateral end surface 510e of the cutting component 502. A locking or set screw can be threaded through a bore 524 of the first end portion 520a and through the split T-extension 522 to lock the connection. The locking screw 526 can include an enlarged head 528 received in a corresponding recess 527 of the connector 520. Similarly, FIG. 7D illustrates a rectangular slot 511 slidably receiving a corresponding rectangular end 521 of the first portion 520a. A locking screw can be threaded through a bore first end portion 520a and into a corresponding threaded hole 513 at the base of the rectangular slot 511. It will be appreciated that other slidable, snap or quick connect with locking options can be used to removably interconnect and lock the cutting component 502 and the guiding component 530 therebetween. The distal cut is performed with the cutting guide 500 assembled on the distal humerus.

Figure 8A:
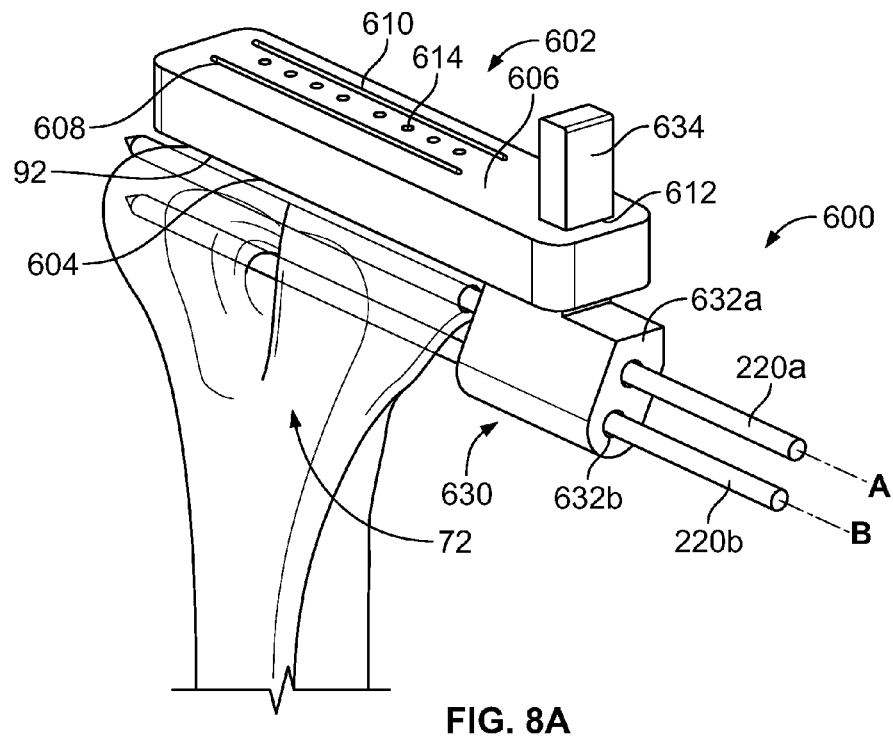
FIGS. 8A and 8B are environmental perspective views illustrating a cutting guide supported on first and second lateral pins for performing an anterior cut and an angled posterior cut according to the present teachings.
Figure 8B:
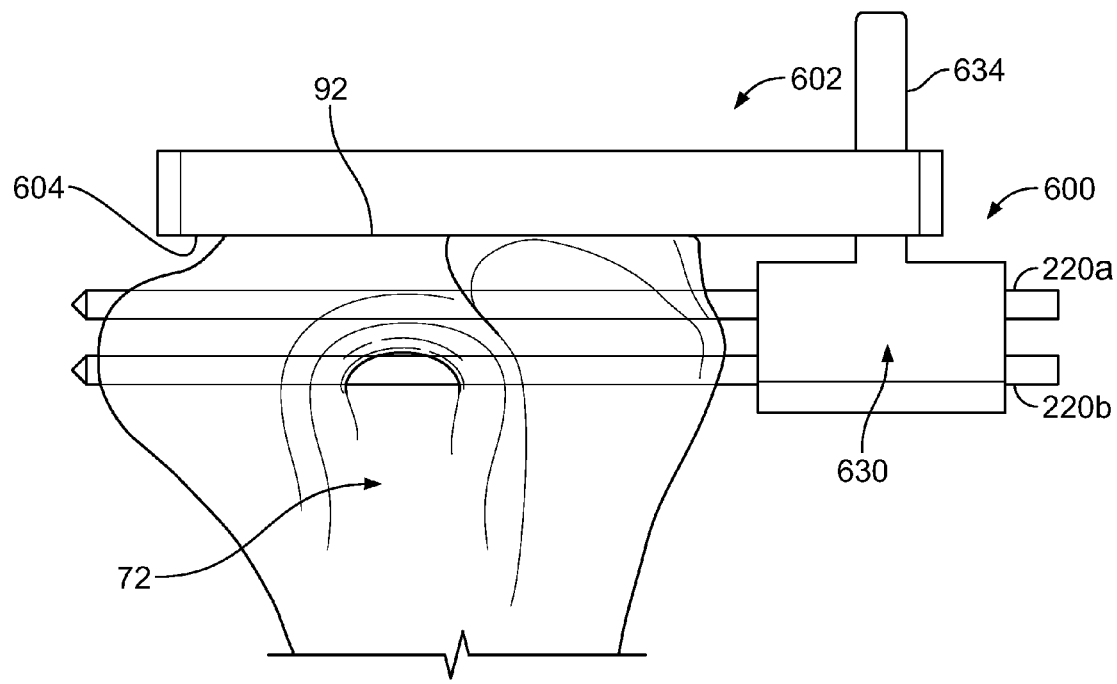
Figure 8C:
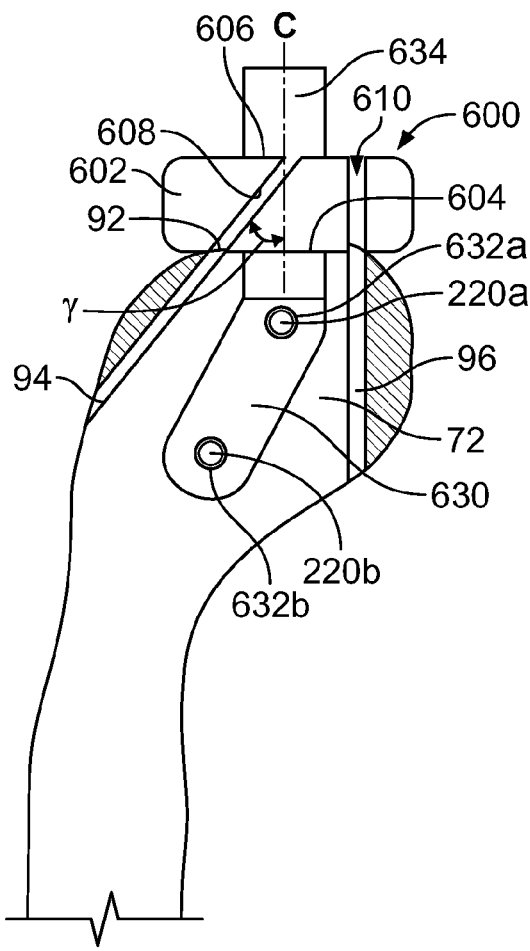
FIG. 8C is an environmental sectional view illustrating a cutting guide supported on a distal resected surface and mounted on first and second lateral pins for performing an anterior cut and an angled posterior cut and the corresponding anterior and angled posterior cuts according to the present teachings.
Figure 9:
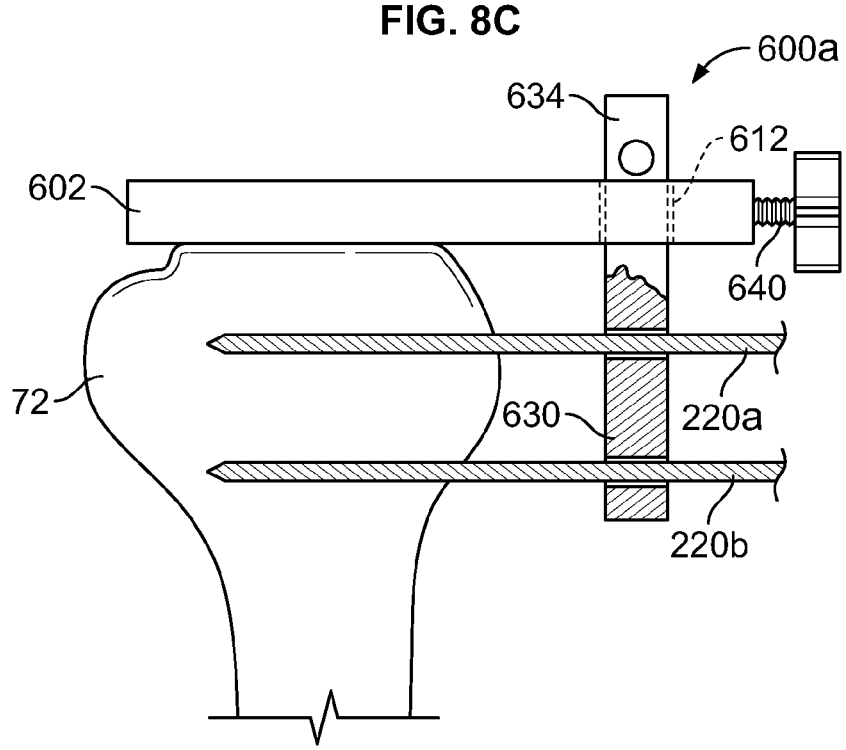
FIG. 9 is an environmental sectional view illustrating a cutting guide supported on distal resected surface and mounted on first and second lateral pins for performing an anterior cut and an angled posterior cut after according to the present teachings.

Referring to FIGS. 8A-8C and 9, after a distal cut is made using the posterior cutting guide 500, the posterior cutting guide 500 can be slid off or otherwise removed from the first and second alignment pins 220a, 220b. A distal cutting guide 600 (FIGS. 8A-8C) or 600a, FIG. 9) can be mounted over the first and second alignment pins 220a, 220b on the distal resected surface 92 of the distal humerus 72. The distal cutting guide 600 can be made as an integral (monolithic) unit or can be modular including a cutting component 602 and a guiding component 630, as illustrated in FIGS. 8A-8C. The guiding component 630 can include first and second guiding bores 632a, 632b for slidably receiving the first and second alignment pins 220a, 220b. The guiding component 630 can also include an extension 634 for removably supporting the cutting component 602. The extension 634 can be oriented along a third axis C that is substantially perpendicular to the direction of the first and second parallel axes A and B of the alignment pins 220a, 220b. The distal cutting guide 600a of FIG. 9 includes a set screw 640 for locking the cutting component 602 to the guiding component 630.

The cutting component 602 can be shaped as a cutting block and include a first surface or bone engagement surface 604 and an opposite or second surface 606. The bone engagement surface 604 is substantially planar or flat for positioning the cutting component 602 on the distal resected surface 92 of the distal humerus 72. The cutting component 602 can include a first elongated planar slot 608 oriented perpendicularly to or at any desired angle relative to the bone engagement surface 604 and a second elongated planar slot 610 at an oblique angle relative to the bone engagement surface 604 for guiding, respectively, a posterior angled cut 94 and an anterior cut 96. As illustrated in FIG. 8C, the first elongated planar slot 608 and the corresponding posterior angled cut 94 are oriented at an oblique angle γ relative to the third axis C. The angle γ is an acute angle, as illustrated in FIG. 8C. The second elongated planar slot 610 and the corresponding anterior cut 96 are oriented parallel to the third axis C and perpendicular to the first and second surfaces 604, 606. The cutting component 602 can include an opening 612 slidably receiving the extension 634 for coupling the cutting component 602 to the guiding component 630 and orienting the first and second elongated slots 608, 610 and the corresponding posterior angled cut 94 and anterior cut 96 in pre-planned orientations and positions relative to the first axis A, which is an anatomic axis for the elbow joint, as discussed above. The opening 612 and the cross-section of the extension 634 can be mating and keyed or have mating non-rotatable shapes, e.g., rectangular, oval or polygonal. In other embodiments, the opening 612 can have a circular or other rotatable shape. The cutting component 602 can also include a plurality of holes 614 for securing the cutting component 602 to the bone during resection.

Figure 10:
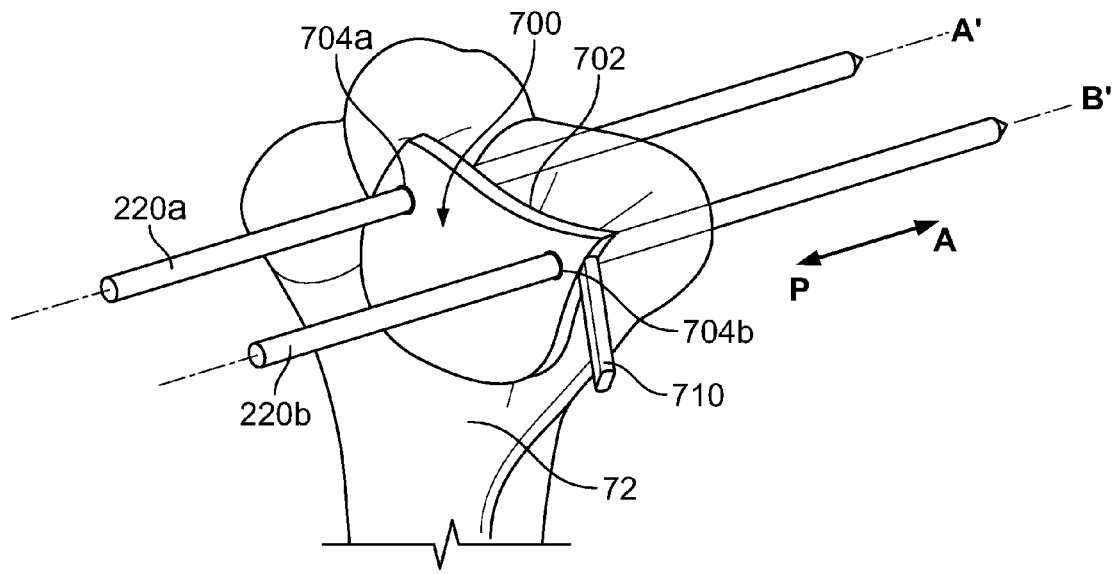
FIG. 10 is an environmental perspective view of a patient-specific alignment guide with first and second posterior pins illustrated for the distal humerus according to the present teachings.
Figure 11:
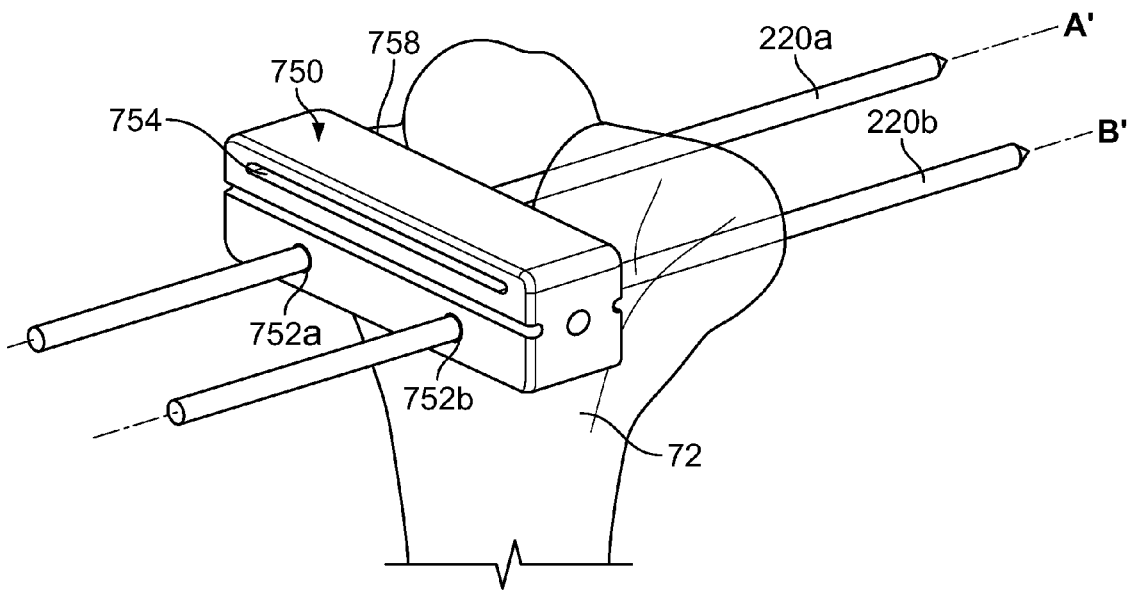
FIG. 11 is an environmental perspective view of a cutting guide supported on first and second posterior pins for performing a distal cut according to the present teachings.

In the procedures described above in connection with FIGS. 5-9, the first and second alignment pins 220a, 220b were placed through the lateral surface of the distal humerus 72 extending from the lateral toward the medial direction. It is also possible to place the first and second alignment pins 220a, 220b posteriorly, i.e., from the posterior toward the anterior surface of the distal humerus 72, as illustrated in FIGS. 10-12. It will be appreciated that the selected axes A' and B' are different anatomic or reference axes than the first and second axes A and B and are oriented in the posterior-anterior direction. The axes A' and B' can be perpendicular to or at any other oblique angle relative to the rotation axis of the elbow joint. As described above, a patient-specific alignment guide 700 can assist in the placement of the first and second alignment pins 220a, 220b. The patient-specific alignment guide 700 includes a three-dimensional patient-specific engagement surface 702 for the posterior surface of the distal humerus 72, and a first and second guiding bores 704a, 704b designed during a preoperative planning stage and based on the patient's anatomy for orienting the first and second alignment pins 220a, 220b along predetermined directions of axes A' and B'. The patient-specific alignment guide 700 can also include a removable or permanently attached handle 710. Similar handles can be used with the other patient-specific alignment guides described herein.

Referring to FIG. 11, after the patient-specific alignment guide 700 is removed, a posterior resection/cutting guide 750 can be removably mounted over the first and second alignment pins 220a, 220b through corresponding apertures 752a, 752b. The posterior cutting guide 700 can include an elongating slot 754 for guiding the distal cut of the distal humerus 72. In another embodiment, the posterior cutting guide 750 can be combined with the patient-specific alignment guide 700, either integrally or by a modular connection (dovetail, T-slot, etc.). In this regard, the combined cutting/alignment guide 700/750 can then engage the posterior surface of the distal humerus 72 with an engagement surface 758 which is patient-specific.

Referring to FIG. 12, after the distal cut is made, the posterior cutting guide 750 is removed and a distal cutting guide 800 is mounted on the resected distal surface of the distal humerus. Similarly to the distal cutting guide 600 discussed above in connection with FIGS. 8A-8C, the distal cutting guide 800 can include a cutting component 802 and a guiding component 830 with first and second bores 832a, 832b for slidably receiving the first and second alignment pins 220a, 220b. The cutting component 802 can include a first elongated planar slot 808 oriented obliquely relative to the reference axes A', B;' and a second elongated planar slot 810 oriented perpendicularly relative to the reference axes A', B;' for guiding, respectively, a posterior angled cut 94 and an anterior cut 96 (see FIG. 8C for exemplary cuts 94, 96). The cutting component 802 can include an opening 812 slidably receiving an extension 834 of the guiding component 830 and orienting the first and second elongated slots 808, 810 and the corresponding posterior angled cut 94 and anterior cut 96 in pre-planned orientations and positions relative to the reference axes A', B'. The opening 812 can be elongated to allow adjustment in the direction of the reference axes A' and B' and can be secured, after adjustment, with a blocking stop inserted in the opening 812 or with pins through the holes 814. It will be appreciated that a complete posterior angled cut 94 can be obstructed by the guiding component 830 in this configuration. Accordingly, after the posterior angled cut is initiated or partially resected, the entire cutting guide 800 and the first and second alignment pins 220a, 220b can be removed and the posterior angled cut 94 finished with a saw blade. Alternatively, the guiding component 830 the first and second alignment pins 220a, 220b can be removed while the cutting component 802 remains secured on the bone with pins through the holes 814 in its original mounted position defined by the first and second alignment pins 220a, 220b.

Referring to FIG. 13, a patient-specific alignment guide 850 is illustrated. The patient-specific alignment guide 850 is specific to the olecranon 88 of proximal ulna 76 of the patient and includes a three-dimensional engagement surface 852, custom-made by computer imaging to conform and nest to a corresponding portion of a patient's olecranon 88. The alignment guide 850 can include a guiding feature 854, computer modeled to be aligned with an anatomic axis A" of the elbow joint 70 of the patient. The guiding feature 854 can be a tubular or partially tubular structure with an elongated guiding bore 856 for guiding an alignment pin 220 into the proximal ulna 76 when the alignment guide 850 is mounted on the olecranon 88. Because of the patient-specific nature of the engagement surface 852, the alignment guide 850 can fit in a unique position/orientation over the olecranon 88 and automatically align the guiding bore 856 along the anatomic axis A". The alignment pin 220 can be used to reference the anatomic axis A" for additional bone preparation after the alignment guide 850 is removed.

Figure 14A:
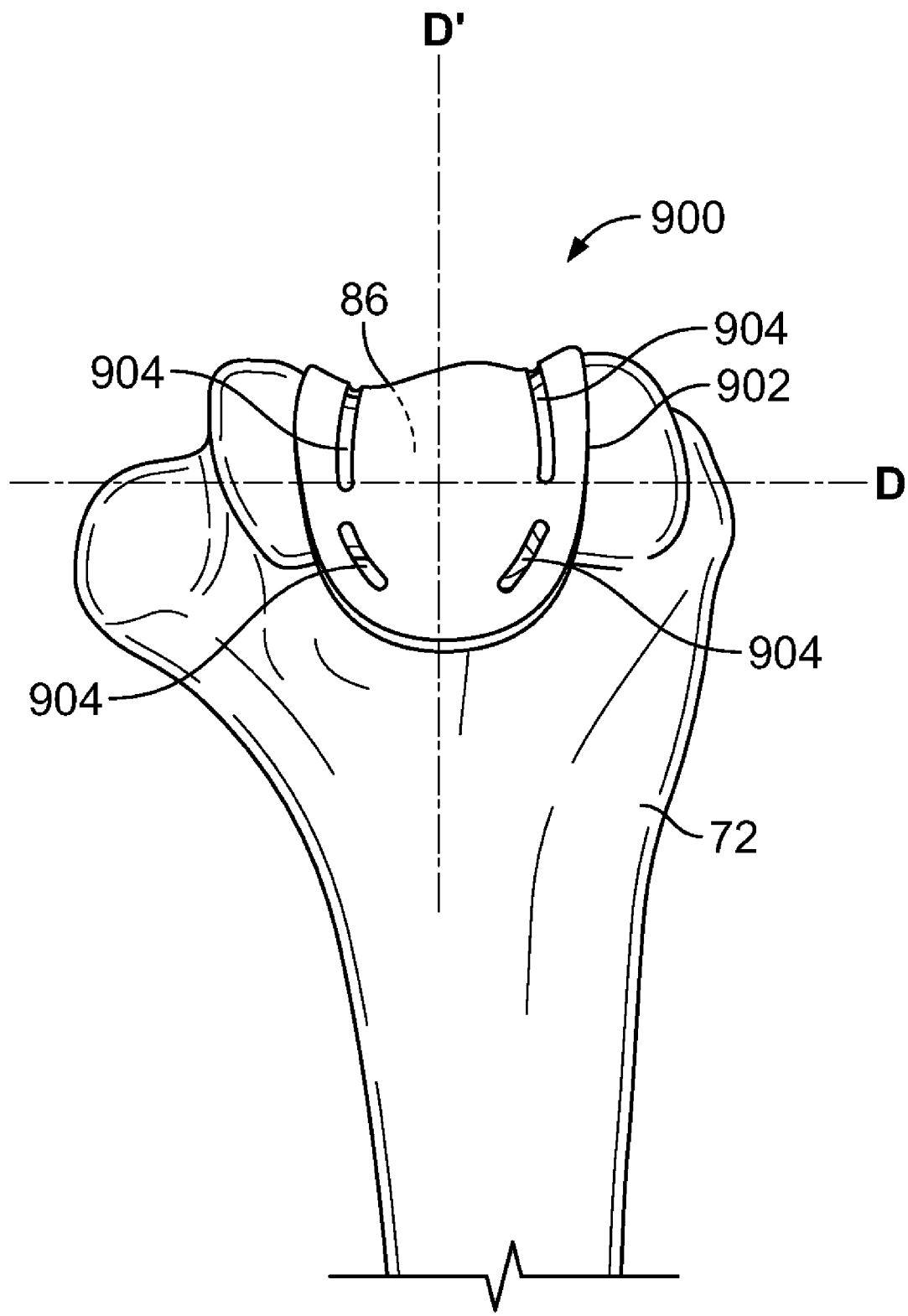
FIG. 14A is an environmental sectional view of a patient-specific alignment guide illustrated for the olecranon fossa of the distal humerus of an elbow joint according to the present teachings.

Referring to FIG. 14A, a patient-specific posterior guide 900 for the olecranon fossa 86 of the distal humerus 72 is illustrated. The patient-specific guide 900 includes a three-dimensional engagement surface 902, custom-made by computer imaging to conform to a corresponding portion of a patient's olecranon fossa 86 (see FIG. 1B). The posterior guide 900 is designed to reference an axis of rotation D and an intramedullary axis D'. The posterior guide can include a plurality of elongated saw blade slots 904 for resecting the trochlea (see FIG. 1A) in preparation for a humeral implant. The guide 900 can be secured to the bone with one or more pins.

Figure 14B:
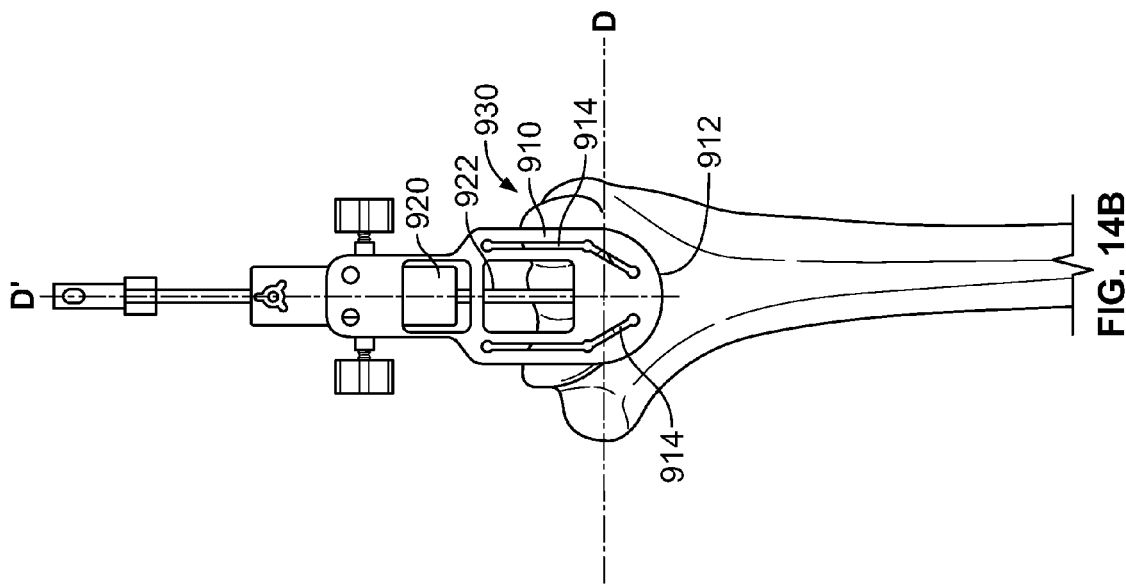
FIG. 14B is an environmental perspective view of a patient-specific cutting guide illustrated for the olecranon fossa of the distal humerus according to the present teachings.

Referring to FIG. 14B, a modular posterior guide 930 for the olecranon fossa 86 of the distal humerus 72 is illustrated. The modular posterior guide 900 is designed to reference an axis of rotation D and an intramedullary axis D'. The modular posterior guide 930 includes a patient specific cutting guide 910 removable coupled to a guiding component 920. The patient specific cutting guide 910 includes a three-dimensional engagement surface 912, custom-made by computer imaging to conform to a corresponding portion of a patient's olecranon fossa 86 (see FIG. 1B). The cutting guide 910 can include a plurality of elongated saw blade slots 914 for resecting the trochlea (see FIG. 1A) in preparation for a humeral implant. The cutting guide 910 is coupled to the guiding component 920 which is supported on the distal humerus with a rod or pin 922 along the intramedullary axis D'. Because of the patient-specific nature of the engagement surface 912, the cutting guide 910 can fit in a unique position/orientation over the olecranon fossa 86 and automatically align the rod 922 along the anatomic axis D'.

Figure 15:
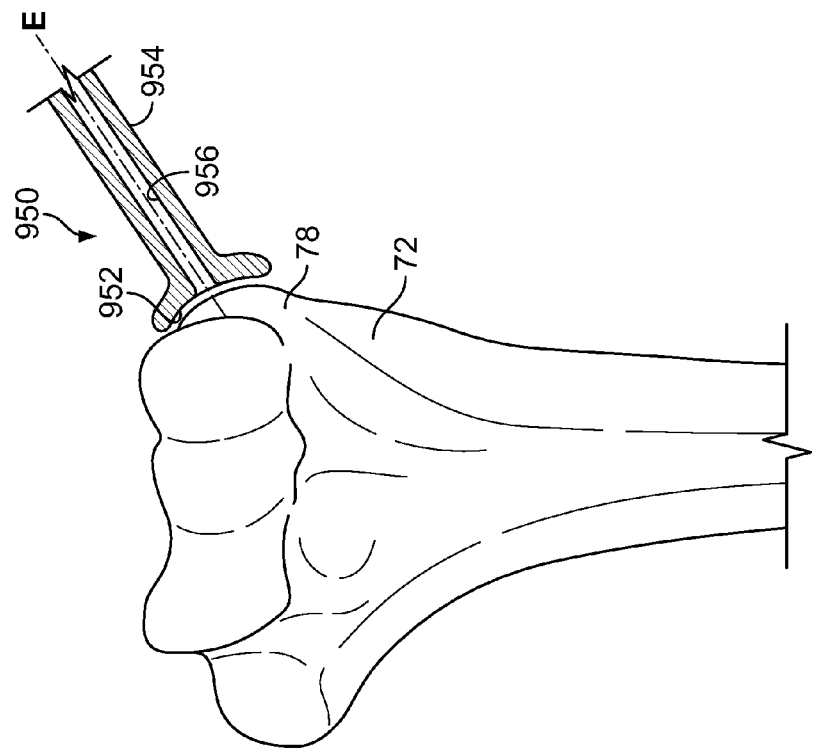
FIG. 15 is an environmental sectional view of a patient-specific guide illustrated for the capitellum of the distal humerus according to the present teachings.

Referring to FIG. 15, a patient-specific alignment guide 950 is illustrated. The patient-specific alignment guide 950 is specific to the capitellum 78 of the distal humerus 72 of the patient and includes a three-dimensional engagement surface 952, custom-made by computer imaging to conform to a patient's capitellum 78 (or portion thereof). The alignment guide 950 can include a guiding feature 954 including an elongated guiding bore 956 for an alignment pin 220 (similar to the pin shown in FIG. 12), computer modeled to be aligned with an anatomic axis E of the elbow joint, such as an axis center on and perpendicular to the surface of the capitellum. The alignment pin 220 can be used to reference the anatomic axis E for additional bone preparation after the alignment guide 950 is removed.

The various patient-specific alignment guides can be made of any biocompatible material, including, polymer, ceramic, metal or combinations thereof. The patient-specific alignment guides can be disposable and can be combined or used with reusable non patient-specific cutting and guiding components.

The foregoing discussion discloses and describes merely exemplary arrangements of the present teachings. Furthermore, the mixing and matching of features, elements and/or functions between various embodiments is expressly contemplated herein, so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the present teachings without departing from the essential scope thereof. One skilled in the art will readily recognize from such discussion, and from the accompanying drawings and claims, that various changes, modifications and variations can be made therein without departing from the spirit and scope of the present teachings as defined in the following claims.

What is claimed is:

1. A method of preparing an elbow joint for an implant, the method comprising:
    mounting a patient-specific alignment guide including a three-dimensional engagement surface custom-made by computer imaging to a corresponding closely conforming bone portion of a distal humerus of a patient's elbow joint;
    inserting into the distal humerus a first pin along an anatomic axis of the elbow joint through a first longitudinal guiding bore of the patient-specific alignment guide;
    inserting into the distal humerus a second pin through a second longitudinal guiding bore of the patient-specific alignment guide, the first and second longitudinal guiding bores being parallel to one another;
    removing the patient-specific alignment guide without removing the first and second pins;
    mounting a first resection guide on the distal humerus of the patient, wherein the first resection guide includes a first cutting component, a first guiding component and an L-shaped connector coupling the first cutting component to the first guiding component;
    abutting the first cutting component against a posterior surface of the distal humerus of the patient such that first and second elongated cutting slots of the first cutting component are aligned along a medial-lateral direction of the distal humerus;
    sliding the first guiding component over the first and second pins and abutting a lateral side of the distal humerus; and
    resecting the distal humerus through one of the first and second elongated cutting slots and forming a distal cut surface for receiving an implant.

2. The method of claim 1, further comprising:
    removing the first resection guide;
    slidably mounting a second guiding component of a second resection guide over the first and second pins;
    supporting a second cutting component of the second resection guide on the distal cut surface;
    mounting the second cutting component over an extension of the second cutting guide, the extension oriented perpendicularly to the first and second guide pins;
    making an anterior cut of the distal humerus through an elongated planar anterior cutting slot of the second cutting component; and
    making a posterior angled cut of the distal humerus through an elongated planar posterior cutting slot of the second cutting component.

3. The method of claim 2, wherein the extension is received non-rotationally in an opening of the second cutting component.

4. The method of claim 3, wherein the opening is elongated.

5. The method of claim 4, wherein the extension is an elongated bar with an elongated cross-section.

6. The method of claim 2, wherein the L-shaped connector is removably coupled to the first cutting component using a T-slot connection.

7. The method of claim 2, wherein the L-shaped connector is removably coupled to the first cutting component using a rectangular slot and locking screw connection.

8. The method of claim 2, wherein the anterior planar cutting slot is perpendicular to a surface of the second cutting guide that contacts the distal cut surface.

9. The method of claim 8, wherein the posterior planar cutting slot is at an oblique angle to the surface of the second cutting guide that contacts the distal cut surface.

10. The method of claim 1, wherein the first and second elongated slots are aligned along preoperatively determined patient specific orientations when the first guiding component is mounted over the first and second pins.

11. The method of claim 1, wherein the first guiding component includes first and second planar portions defining an acute angle therebetween.

12. The method of claim 11, further comprising mounting the first and third guiding bores over the first and second pins for a right humerus.

13. The method of claim 11, wherein the first guiding component includes first, second and third parallel guiding bores.

14. The method of claim 13, further comprising mounting the first and second guiding bores over the first and second pins for a left humerus.

15. A method of preparing an elbow joint for an implant, the method comprising:
    mounting a patient-specific alignment guide including a three-dimensional engagement surface custom-made by computer imaging to a corresponding closely conforming portion of a distal humerus portion of a patient's elbow joint;
    inserting into the distal humerus a first pin through a first longitudinal guiding bore of the patient-specific alignment guide along a medial-lateral direction;
    inserting into the distal humerus a second pin through a second longitudinal guiding bore of the patient-specific alignment guide, the first and second longitudinal guiding bores being parallel to one another;
    removing the patient-specific alignment guide without removing the first and second pins;
    abutting a first cutting component against a posterior surface of the distal humerus of the patient such that first and second elongated cutting slots of the first cutting component are aligned along a medial-lateral direction of the distal humerus;
    coupling the first cutting component to a first guiding component using an L-shaped connector;

sliding the first guiding component over the first and second pins and abutting a lateral side the distal humerus; and resecting the distal humerus through one of the first and second elongated cutting slots and forming a distal cut surface for receiving an implant.

16. The method of claim 15, further comprising:

removing the first cutting component and the first guiding component without removing the first and second pins;

slidably mounting a second guiding component over the first and second pins;

supporting a second cutting component on the distal cut surface;

making an anterior cut of the distal humerus through an elongated planar anterior cutting slot of the second cutting component; and making a posterior angled cut of the distal humerus through an elongated planar posterior cutting slot of the second cutting component.

17. The method of claim 16, further comprising passing an extension of the second guiding component through an elongated opening of the second cutting guide.

18. The method of claim 16, wherein the anterior planar cutting slot is perpendicular to a surface of the second cutting guide that contacts the distal cut surface.

19. The method of claim 18, wherein the posterior planar cutting slot is at an oblique angle to the surface of the second cutting guide that contacts the distal cut surface.

* * * * *

UNITED STATES PATENT AND TRADEMARK OFFICE
CERTIFICATE OF CORRECTION

PATENT NO. : 8,377,066 B2  Page 1 of 1
APPLICATION NO. : 12/888005
DATED : February 19, 2013
INVENTOR(S) : Nicholas J. Katrana et al.

It is certified that error appears in the above-identified patent and that said Letters Patent is hereby corrected as shown below:

On Title Page 7, References Cited, Other Publications, Column 1, line 19, (Information Disclosure Statement dated January 26, 2012, Form 1449, page 2, Non Patent Literature Documents, Reference No. CD), After "DE102009028503.2", insert --,--.

On Title Page 7, References Cited, Other Publications, Column 1, line 35, (Information Disclosure Statement dated July 7, 2011, Form 1449, page 16, Non Patent Literature Documents, Reference No. CC), After "Inc.", insert --,--.

On Title Page 7, References Cited, Other Publications, Column 2, line 4, (Information Disclosure Statement dated July 7, 2011, Form 1449, page 16, Non Patent Literature Documents, Reference No. CG), After "Inc.", insert --,--.

On Title Page 7, References Cited, Other Publications, Column 2, line 20, (Information Disclosure Statement dated July 7, 2011, Form 1449, page 16, Non Patent Literature Documents, Reference No. CN), After "Inc.", insert --,--.

In the Claims

Column 11, Line 35, Claim 1 (Claims Page 2, Line 5, Claim 2, Amendment/Request Reconsideration – After Non-Final Rejection filed July 11, 2012); In Claim 1, before "portion", delete "bone".

Signed and Sealed this
Thirteenth Day of May, 2014

Michelle K. Lee
*Deputy Director of the United States Patent and Trademark Office*